United States Patent
Kimura

(10) Patent No.: US 10,663,552 B2
(45) Date of Patent: May 26, 2020

(54) MAGNETIC RESONANCE IMAGING APPARATUS THAT DIVIDES IMAGING REGION TEMPORALLY OR SPATIALLY AND ACQUIRES DATA THEREOF USING DIFFERENT READOUT SEQUENCES

(71) Applicant: TOSHIBA MEDICAL SYSTEMS CORPORATION, Otawara-shi (JP)

(72) Inventor: Tokunori Kimura, Tochigi (JP)

(73) Assignee: TOSHIBA MEDICAL SYSTEMS CORPORATION, Otawara-Shi, Tochigi-Ken (JP)

(*) Notice: Subject to any disclaimer, the term of this patent is extended or adjusted under 35 U.S.C. 154(b) by 1163 days.

(21) Appl. No.: 14/872,319

(22) Filed: Oct. 1, 2015

(65) Prior Publication Data

US 2016/0018501 A1    Jan. 21, 2016

Related U.S. Application Data

(63) Continuation of application No. PCT/JP2014/059897, filed on Apr. 3, 2014.

(30) Foreign Application Priority Data

Apr. 4, 2013   (JP) ................. 2013-078873

(51) Int. Cl.
  *G01R 33/563*   (2006.01)
  *A61B 5/055*   (2006.01)
  (Continued)

(52) U.S. Cl.
  CPC ........ *G01R 33/5635* (2013.01); *A61B 5/0042* (2013.01); *A61B 5/055* (2013.01);
  (Continued)

(58) Field of Classification Search
  USPC .................. 324/300–322; 600/407–435; 382/128–131
  See application file for complete search history.

(56) References Cited

U.S. PATENT DOCUMENTS 6,564,080 B1   5/2003   Kimura .................. 600/410
7,898,254 B2 *  3/2011   Feinberg ............ G01R 33/4818
                                                      324/309

(Continued)

FOREIGN PATENT DOCUMENTS

CN   101138497 A    3/2008
JP   62-253043    11/1987
(Continued)

OTHER PUBLICATIONS

Chinese office action dated Jun. 2, 2017, in Patent Application No. CN 201480018888.X.

(Continued)

*Primary Examiner* — Daniel R Miller
(74) *Attorney, Agent, or Firm* — Nixon & Vanderhye P.C.

(57) ABSTRACT

A magnetic resonance imaging apparatus according to an embodiment includes a dividing unit, an acquiring unit, and a combining unit. The dividing unit is configured to divide an imaging region of a patient into at least two temporal or spatial ranges. Of the temporal or spatial ranges, the acquiring unit is configured to perform a data acquiring process on a first range by using a first readout sequence and to perform a data acquiring process on a second range by using a second readout sequence that is different from the first readout sequence in terms of one or both of the type of sequence and an imaging condition. The combining unit is configured to combine an image generated from data acquired by using the first readout sequence with an image generated from data acquired by using the second readout sequence.

16 Claims, 19 Drawing Sheets

(51) Int. Cl.
*G01R 33/56* (2006.01)
*A61B 5/00* (2006.01)
*G01R 33/561* (2006.01)

(52) U.S. Cl.
CPC ........ *A61B 5/7425* (2013.01); *G01R 33/5608* (2013.01); *G01R 33/5613* (2013.01); *G01R 33/5614* (2013.01); *G01R 33/56308* (2013.01); *G01R 33/56366* (2013.01); *A61B 2576/026* (2013.01); *G01R 33/5602* (2013.01); *G01R 33/5607* (2013.01); *G01R 33/56333* (2013.01)

(56) References Cited

U.S. PATENT DOCUMENTS

| | | | | |
|---|---|---|---|---|
| 8,131,034 | B2 * | 3/2012 | Gunther | G01R 33/56366 382/128 |
| 8,159,221 | B2 * | 4/2012 | Yui | G01R 33/5614 324/307 |
| 8,624,591 | B2 | 1/2014 | Kimura | 324/306 |
| 8,664,954 | B2 * | 3/2014 | Hetzer | G01R 33/4818 324/309 |
| 9,759,797 | B2 * | 9/2017 | Li | G01R 33/56509 |
| 2008/0071166 | A1 | 3/2008 | Miyazaki | 600/419 |
| 2009/0134871 | A1 * | 5/2009 | Yui | G01R 33/5614 324/309 |
| 2010/0277169 | A1 * | 11/2010 | Feiweier | G01R 33/4818 324/307 |
| 2012/0013336 | A1 * | 1/2012 | Hetzer | G01R 33/4818 324/309 |
| 2016/0018501 | A1 * | 1/2016 | Kimura | A61B 5/055 324/322 |

FOREIGN PATENT DOCUMENTS

| | | |
|---|---|---|
| JP | 5-123314 | 5/1993 |
| JP | 2000-237163 | 9/2000 |
| JP | 2001-252263 | 9/2001 |
| JP | 2002-253527 | 9/2002 |
| JP | 2006-304818 | 11/2006 |
| JP | 2008-86748 | 4/2008 |
| JP | 2013-34549 | 2/2013 |

OTHER PUBLICATIONS

Edelman et al., "Qualitative Mapping of Cerebral Blood Flow and Functional Localization with Echo-planar MR Imaging and Signal Targeting with Alternating Radio Frequency", *Radiology*, vol. 192, No. 2, Aug. 1994, pp. 513-519.

Kimura, Non-invasive Perfusion Imaging by Modified STAR Using Asymmetric Inversion Slabs (ASTAR), *Japanese Journal of Magnetic Resonance in Medicine* 20(8), 2001, pp. 374-385—with an English-language Abstract.

Kwong et al., "MR Perfusion Studies with $T_1$-Weighted Echo Planar Imaging", *Magn. Reson. Med.* 1995, pp. 878-887.

Mani et al., "Background Suppression with Multiple Inversion Recovery Nulling: Applications to Projective Angiography", *Magn. Reson. Med.*, vol. 37, 1997, pp. 898-905.

Wells et al., In Vivo Hadamard Encoded Continuous Arterial Spin Labeling (H-CASL), *Magn. Reson. Med.*, vol. 63, 2010, pp. 1111-1118.

International Search Report for PCT/JP2014/059897 dated Jul. 1, 2014, four pages.

* cited by examiner tag image − control image = ASL image imaging slab arterial blood flow

COMBINED MRA IMAGE

MAGNETIC RESONANCE IMAGING APPARATUS THAT DIVIDES IMAGING REGION TEMPORALLY OR SPATIALLY AND ACQUIRES DATA THEREOF USING DIFFERENT READOUT SEQUENCES

CROSS-REFERENCE TO RELATED APPLICATIONS

This application is a continuation of PCT international application Ser. No. PCT/JP2014/059897 filed on Apr. 3, 2014 which designates the United States, incorporated herein by reference, and which claims the benefit of priority from Japanese Patent Application No. 2013-078873, filed on Apr. 4, 2013, the entire contents of which are incorporated herein by reference.

FIELD

Embodiments described herein relate generally to a magnetic resonance imaging apparatus.

BACKGROUND

Conventionally, various types of readout sequences that can be included in a pulse sequence used by Magnetic Resonance Imaging (MRI) apparatuses can roughly be categorized into a Spin Echo (SE) based pulse sequence and a Field Echo (FE) (or Gradient Echo (GRE)) based pulse sequence. Further, the FE based pulse sequence includes a Fast Low-Angle Shot (FLASH) based pulse sequence and a Steady State Free Precession (SSFP) based pulse sequence. Generally speaking, those readout sequences are known to have such characteristics that the former has a lower Signal-to-Noise Ratio (SNR) per unit acquisition period but is more resistant to non-uniformity (distortions or missing signals) of the magnetic field, whereas the latter has a higher SN ratio per unit acquisition period but is less resistant to non-uniformity of the magnetic field. For this reason, operators of magnetic resonance imaging apparatus selectively use different types of readout sequences and imaging conditions, as appropriate, in accordance with the site serving as the imaged target and the imaging purpose, with knowledge of the characteristics of each of the readout sequences.

DETAILED DESCRIPTION

A magnetic resonance imaging (MRI) apparatus according to an embodiment includes a dividing unit, an acquiring unit, and a combining unit. The dividing unit is configured to divide an imaging region of a patient into at least two temporal or spatial ranges. Of the temporal or spatial ranges, the acquiring unit is configured to perform a data acquiring process on a first range by using a first readout sequence and to perform a data acquiring process on a second range by using a second readout sequence that is different from the first readout sequence in terms of one or both of the type of sequence and an imaging condition. The combining unit is configured to combine an image generated from data acquired by using the first readout sequence with an image generated from data acquired by using the second readout sequence.

In one example embodiment processing circuitry is configured to divide an imaging region of a patient into at least two temporal ranges, perform a data acquiring process on a first range of the temporal ranges by using a first readout sequence and perform a data acquiring process on a second range of the temporal ranges by using a second readout sequence that is different from the first readout sequence in terms of one or both of a type of sequence and an imaging condition, and combine an image generated from data acquired by using the first readout sequence with an image generated from data acquired by using the second readout sequence.

Exemplary embodiments of an MRI apparatus will be explained in detail below, with reference to the accompanying drawings.

First Embodiment

Figure 1:
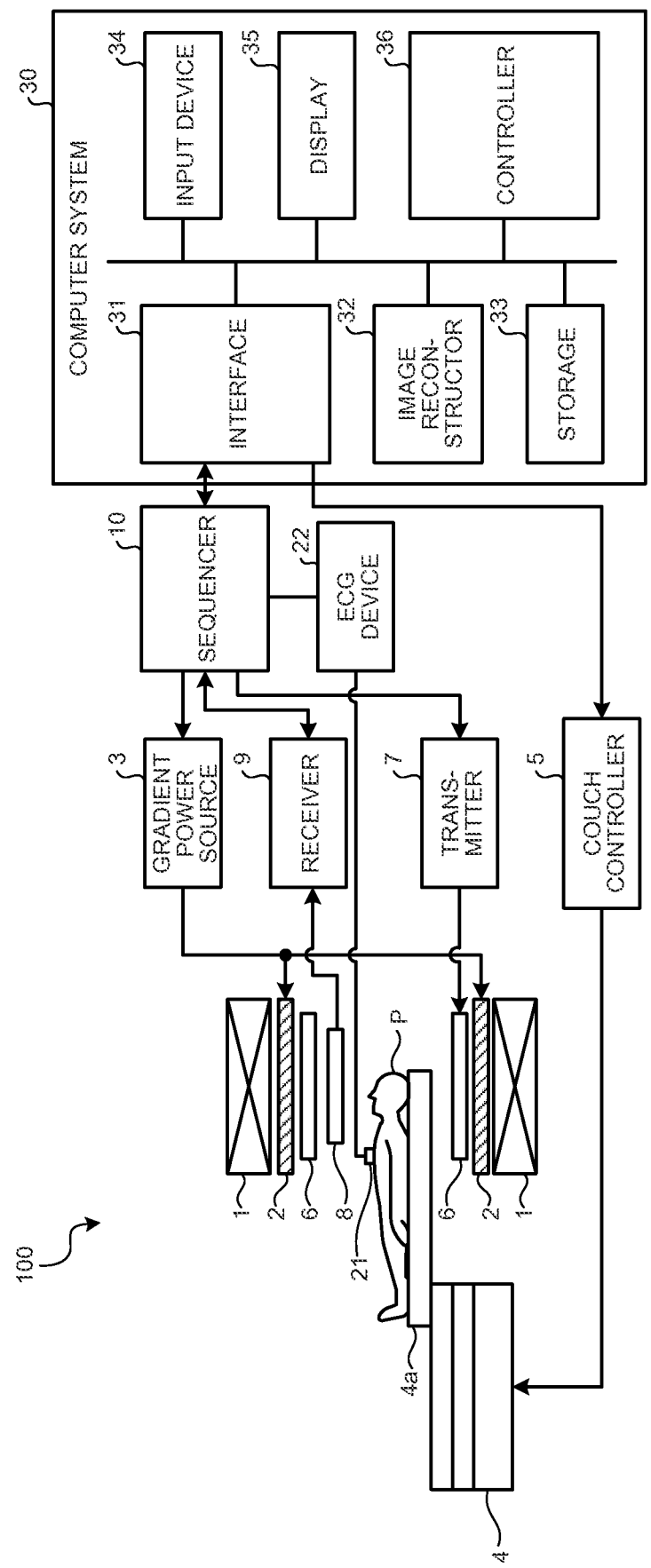
FIG. 1 is a diagram of an exemplary configuration of an MRI apparatus according to a first embodiment.

To begin with, a first embodiment will be explained. FIG. 1 is a diagram of an exemplary configuration of an MRI apparatus according to the first embodiment. As illustrated in FIG. 1, an MRI apparatus 100 includes a static magnetic field magnet 1, a gradient coil 2, a gradient power source 3, a couch 4, a couch controller 5, a transmission Radio Frequency (RF) coil 6, a transmitter 7, a reception RF coil 8, a receiver 9, a sequencer 10, an Electrocardiogram (ECG) sensor 21, an ECG device 22, and a computer system 30.

The static magnetic field magnet 1 is a magnet formed in the shape of a hollow circular cylinder and is configured to generate a uniform static magnetic field in the space on the inside thereof. The static magnetic field magnet 1 may be configured by using, for example, a permanent magnet, a superconductive magnet, or the like.

The gradient coil 2 is a coil formed in the shape of a hollow circular cylinder and is disposed on the inside of the static magnetic field magnet 1. The gradient coil 2 is formed by combining three coils corresponding to X-, Y-, and Z-axes that are orthogonal to one another. These three coils individually receive a supply of electric current from the gradient power source 3 (explained later) and generate gradient magnetic fields of which the magnetic field intensities change along the X-, Y-, and Z-axes. It is assumed that the Z-axis direction is the same as the direction of the static magnetic field. The gradient power source 3 is configured to supply the electric current to the gradient coil 2.

In this situation, the gradient magnetic fields on the X-, Y-, and Z-axes that are generated by the gradient coil 2 correspond to, for example, a slice-selecting-purpose gradient magnetic field Gs, a phase-encoding-purpose gradient magnetic field Ge, and a read-out-purpose gradient magnetic field Gr, respectively. The slice-selecting-purpose gradient magnetic field Gs is used for determining an imaging cross-sectional plane in an arbitrary manner. The phase-encoding-purpose gradient magnetic field Ge is used for changing the phase of a magnetic resonance signal according to a spatial position. The read-out-purpose gradient magnetic field Gr is used for changing the frequency of a magnetic resonance signal according to a spatial position.

The couch 4 includes a couchtop 4a on which an examined subject (hereinafter, "patient") P is placed. Under control of the couch controller 5 (explained later), while the patient P is placed thereon, the couchtop 4a is inserted into the hollow (i.e., an imaging opening) of the gradient coil 2. Normally, the couch 4 is provided so that the longitudinal direction thereof extends parallel to the central axis of the static magnetic field magnet 1. The couch controller 5 is a device configured to control the couch 4 under control of a controller 36 and is configured to drive the couch 4 so that the couchtop 4a moves in longitudinal directions and in up-and-down directions.

The transmission RF coil 6 is disposed on the inside of the gradient coil 2 and is configured to receive a supply of a Radio Frequency (RF) pulse from the transmitter 7 and to apply an RF wave to the patient P. The transmitter 7 is configured to transmit the RF wave corresponding to a Larmor frequency to the transmission RF coil 6.

The reception RF coil 8 is disposed on the inside of the gradient coil 2 and is configured to receive magnetic resonance signals emitted from the patient P due to an influence of the RF wave. When having received the magnetic resonance signals, the reception RF coil 8 outputs the received magnetic resonance signals to the receiver 9.

The receiver 9 is configured to generate Magnetic Resonance (MR) data on the basis of the magnetic resonance signals being output from the reception RF coil 8. More specifically, the receiver 9 generates the MR data by applying a digital conversion to the magnetic resonance signals being output from the reception RF coil 8. The MR data is generated as data corresponding to a k-space by keeping information about spatial frequencies in a Phase Encoding (PE) direction, a Read-Out (RO) direction, and a Slice Encoding (SE) direction in correspondence with one another while using the slice-selecting-purpose gradient magnetic field Gs, the phase-encoding-purpose gradient magnetic field Ge, and the read-out-purpose gradient magnetic field Gr described above. Further, when having generated the MR data, the receiver 9 transmits the generated MR data to the sequencer 10. In this situation, the receiver 9 may be provided on a gantry device side where the static magnetic field magnet 1 and the gradient coil 2 are provided.

The sequencer 10 is configured to perform a data acquiring process to generate images of the patient P, by driving the gradient power source 3, the transmitter 7, and the receiver 9, according to sequence execution information transmitted thereto from the computer system 30. The sequencer 10 is, for example, configured with processing circuitry such as a processor such as a Central Processing Unit (CPU) or a Micro Processing Unit (MPU); a memory; an Application Specific Integrated Circuit (ASIC); or a Field Programmable Gate Array (FPGA). In this situation, the sequence execution information is information that defines a pulse sequence used for acquiring the MR data from the patient P. More specifically, the sequence execution information is information defining a procedure for performing the data acquiring process such as the following: the intensity of the power source to be supplied by the gradient power source 3 to the gradient coil 2 and the timing with which the power source is to be supplied; the intensity of the RF signal to be transmitted by the transmitter 7 to the transmission RF coil 6 and the timing with which the RF signal is to be transmitted; and the timing with which the magnetic resonance signals are to be detected by the receiver 9.

As a result of a scan performed on the patient P by driving the gradient power source 3, the transmitter 7, and the receiver 9, when the MR data has been transmitted to the sequencer 10 from the receiver 9, the sequencer 10 transfers the MR data to the computer system 30.

The ECG sensor 21 is attached to the body surface of the patient P and is configured to detect ECG signals indicating heartbeats, a pulse wave, and respiration of the patient P, as electrical signals. The ECG device 22 is configured to generate gate signals by applying various types of processing processes including an A/D conversion process and a delay process to the ECG signals detected by the ECG sensor 21 and to transmit the generated gate signals to the sequencer 10.

The computer system 30 is configured to exercise overall control of the MRI apparatus 100. For example, the computer system 30 performs the data acquiring process, an image reconstructing process, and the like by driving the functional units described above. The computer system 30 includes an interface 31, an image reconstructor 32, a storage 33, an input device 34, a display 35, and the controller 36.

The interface 31 is configured to control transmissions and receptions of various types of signals exchanged between the computer system 30 and the sequencer 10. For example, the interface 31 transmits the sequence execution information to the sequencer 10 and receives the MR data from the sequencer 10. When having received pieces of MR data, the interface 31 stores the pieces of MR data into the storage 33, while keeping the pieces of MR data in correspondence with different patients P.

The image reconstructor 32 is configured to generate image data rendering the inside of the body of the patient P, by applying a post-processing process, i.e., a reconstructing process such as a Fourier transform, to the MR data stored in the storage 33. The reconstructor 32 is, for example, configured with processing circuitry such as a processor such as a Central Processing Unit (CPU) or a Micro Processing Unit (MPU); a memory; an Application Specific Integrated Circuit (ASIC); or a Field Programmable Gate Array (FPGA).

The storage 33 is configured to store therein the MR data received by the interface 31 and the image data generated by the image reconstructor 32 so as to be kept in correspondence with each of different patients P.

The input device 34 is configured to receive various types of instructions and inputs of information from an operator. As the input device 34, it is possible to use, as appropriate, any of pointing devices such as a mouse, a trackball, and the like, any of selecting devices such as a mode changing switch and the like, and/or any of input devices such as a keyboard and the like.

The display 35 is configured to display various types of information such as spectrum data, image data, or the like, under the control of the controller 36. It is possible to use a display device such as a liquid crystal display device, as the display 35.

The controller 36 is configured to exercise overall control of the MRI apparatus 100. The controller 36 is, for example, configured with processing circuitry such as a processor such as a Central Processing Unit (CPU) or a Micro Processing Unit (MPU); a memory; an Application Specific Integrated Circuit (ASIC); or a Field Programmable Gate Array (FPGA). More specifically, the controller 36 controls a scan by generating the sequence execution information on the basis of various types of instructions received from the operator via the input device 34 and transmitting the generated sequence execution information to the sequencer 10, and also, controls the image reconstructing process performed on the basis of the MR data sent from the sequencer 10 as a result of the scan.

The exemplary configuration of the MRI apparatus 100 according to the first embodiment has thus been explained. The MRI apparatus 100 configured as described above is able to take images of the patient by using any of various imaging methods, while using any of various types of readout sequences. In the following explanations, a sequence from the time when an excitation-purpose RF pulse is applied to the time when the magnetic resonance signals are obtained will be referred to as a "readout sequence". In contrast, an overall sequence that includes any of various types of pre-pulses such as a labeling-purpose RF pulse applied prior to the readout sequence as well as the readout sequence will be referred to as a "pulse sequence".

In this situation, conventionally, various types of readout sequences that can be included in a pulse sequence used by MRI apparatuses can roughly be categorized into an SE-based pulse sequence and a FE (GRE) based pulse sequence. Further, the FE-based pulse sequence includes a FLASH-based pulse sequence and an SSFP-based pulse sequence. Generally speaking, those readout sequences are known to have such characteristics that the former has a lower SN ratio per unit acquisition period but is more resistant to non-uniformity (distortions or missing signals) of the magnetic field, whereas the latter has a higher SN ratio per unit acquisition period but is less resistant to non-uniformity of the magnetic field. For this reason, operators of magnetic resonance imaging apparatus selectively use different types of readout sequences and imaging conditions, as appropriate, in accordance with the site serving as the imaged target and the imaging purpose, with knowledge of the characteristics of each of the readout sequences.

For instance, examples of imaging methods implemented by MRI apparatuses include an Arterial Spin Labeling (ASL) method. The ASL method is an imaging method by which blood flows are imaged without a contrast enhancement, by performing a data acquiring process after a predetermined waiting period has elapsed since an RF wave is applied for the purpose of labeling fluid flowing into an imaging region.

Figure 2:
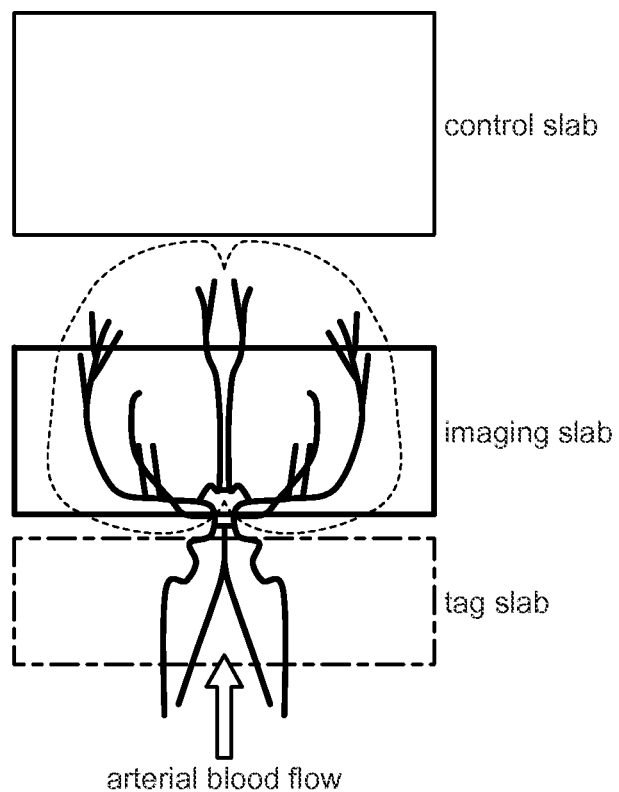
FIG. 2 is a first drawing for explaining an example of a conventional Arterial Spin Labeling (ASL) method.
Figure 3:
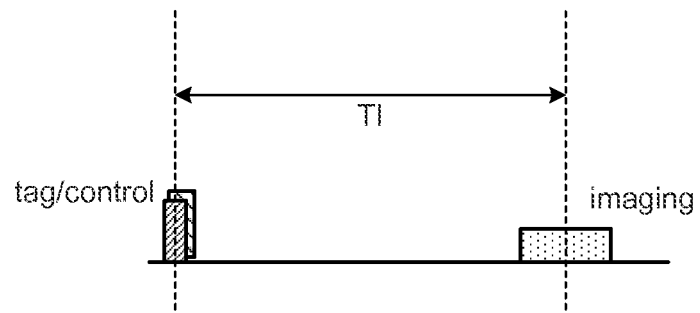
FIG. 3 is a second drawing for explaining the example of the conventional ASL method.
Figure 4:
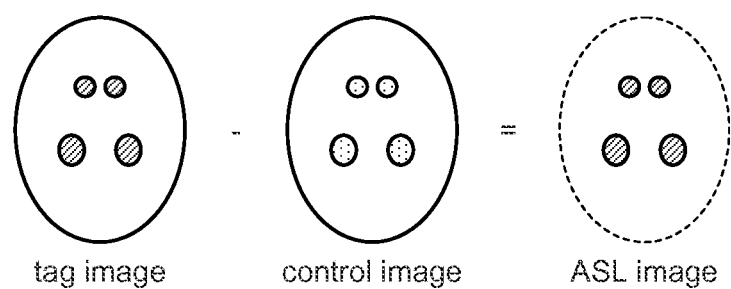
FIG. 4 is a third drawing for explaining the example of the conventional ASL method.

FIGS. 2 to 4 are drawings for explaining a conventional ASL method. Generally speaking, according to the ASL method, in order to inhibit background signals, an image called a tag image and another image called a control image are generated, and further, a difference image between the two images is generated.

For example, as illustrated in FIG. 2, according to the ASL method, an RF wave for the purpose of labeling the blood (arterial blood flow) flowing into an imaging region (imaging slab) is applied to a tag region (tag slab) that is set in a position upstream of the imaging region. After that, as illustrated in FIG. 3, a data acquiring process (imaging) is performed after a predetermined waiting period TI has elapsed since the RF wave (tag) is applied, so as to generate a tag image from acquired data. Further, according to the ASL method, as illustrated in FIG. 2, an RF wave is also applied to a control region (control slab) that is set on the opposite side from the tag region while the imaging region is interposed therebetween. After that, as illustrated in FIG. 3, a data acquiring process (imaging) is performed after a waiting period TI, which is the same as the waiting period used for the data acquiring process of the tag image, has elapsed since the RF wave (control) is applied, so as to generate a control image from acquired data. Subsequently, as illustrated in FIG. 4, an ASL image (ASL image) in which the background signals are inhibited is generated by generating a difference image between the generated tag image (tag image) and the generated control image (control image).

Further, the ASL method may roughly be categorized into an ASL Magnetic Resonance Angiography (ASL-MRA) method and an ASL Magnetic Resonance Perfusion (ASL-MRP) method, depending on the use thereof. The ASL-MRA is a method used for obtaining a blood vessel image, whereas the ASL-MRP is a method used for obtaining a perfusion image. Further, in recent years, such a method is also being used by which the imaging process is performed multiple times while dynamically varying the waiting period from the application of the labeling-purpose RF wave to the data acquiring process, in order to observe temporal changes (hemodynamics) during the ASL-MRA or ASL-MRP procedure.

In this situation, although the ASL-MRA method and the ASL-MRP method both belong to the ASL method in terms of the type of imaging method, the technical points thereof are different. For example, when the ASL-MRA method is used, the number of times of additions can be smaller because the SN ratio for the blood vessels is large, but it is necessary to achieve a time resolution and a spatial resolution. Further, when using the ASL-MRP method, it is possible to obtain an image in which the SN ratio of the blood flow signals is extremely lower (1/1000 or less) than those of the stationary tissues in the background, compared to when the ASL-MRA method is used. Accordingly, when the difference is calculated between the tag image and the control image, a process of equalizing the Magnetization Transfer Contrast (MTC) effect between the two images may be performed, or an arithmetic mean may be calculated multiple times by using a lower matrix. Further, even among ASL-MRP procedures, imaging conditions of readout sequences vary depending on the organ serving as the imaged target, because the blood flow amount is larger for the kidney or the lungs and is smaller for the brain, the prostate, or a muscle.

As another example, in a Three-Dimensional Time-Of-Flight MRA (3D TOF-MRA) method, which is most popularly used in general, the time-of-flight effect of blood vessel flows is used. Accordingly, the thinner an imaging region (an imaging slab) per single imaging process is, the higher the SN ratio will be. For this reason, when the 3D TOF-MRA method is implemented, a multi-slab method is used by which an imaging region is divided into a plurality of sectional regions, so that a data acquiring process is performed on each of the plurality of sectional regions.

Figure 5:
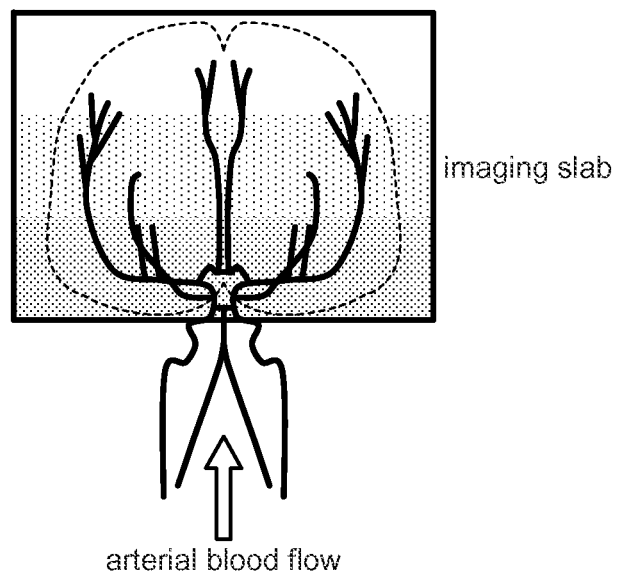
FIG. 5 is a first drawing for explaining conventional Three-Dimensional Time-Of-Flight Magnetic Resonance Angiography (3D TOF-MRA) methods.
Figure 6:
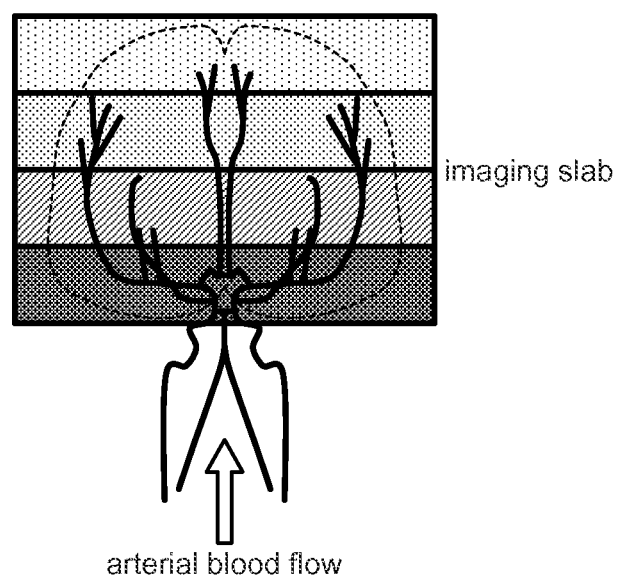
FIG. 6 is a second drawing for explaining the conventional 3D TOF-MRA methods.

FIGS. 5 and 6 are drawings for explaining conventional 3D TOF-MRA methods. FIG. 5 illustrates an example of an imaging process performed by using a single-slab method. FIG. 6 illustrates an example of an imaging process performed by using a multi-slab method.

For example, as illustrated in FIG. 5, when the single-slab method is used, in many situations, a Tilted Optimized Non-saturation Excitation (TONE) method (an Inclined Slab for Contrast Enhancement [ISCE] method) may be used together, by which the RF wave to be radiated onto the imaging region (the imaging slab) is tilted (the longer the distance from the flow-in position is, the shallower the flip angle of the RF wave is). Further, as illustrated in FIG. 6, the TONE method may also be used together with the multi-slab method in some situations. When images of the head are acquired by implementing such a 3D-MRA method, it is a common practice to use an FE (GRE) based readout sequence with which it is possible to obtain an image that has few voids in a major artery part positioned in the vicinity of the circle of Willis (Willis ring).

Further, another imaging method that can be implemented by an MRI apparatus is a diffusion imaging method. When the diffusion imaging method is used, a single-shot Spin-Echo Echo Planar Imaging (SE-EPI) based readout sequence is mainly used. However, for sites having a larger distortion, a Fast Spin Echo (FSE) based readout sequence may also be used. Further, even among EPI methods, the operator selectively uses various options including an Echo Time (TE), an acquisition matrix, a Sensitivity Encoding (SENSE) factor, and the numbers of shots. Furthermore, the operator also selectively uses various options including a Periodically Rotated Overlapping Parallel Lines with Enhanced Reconstruction (PROPELLER) method which differs in the trajectory of the k-space as well as sampling methods based on a radial type, and the like.

Further, it is a recent trend that popularly-used methods include a method for converting various types of MRI-related parameters such as T1, T2, the proton density, an Apparent Diffusion Coefficient (ADC), the blood flow amount, a chemical shift, magnetization susceptibility, temperatures, and the like, not into a parameter-weighted image, but into a quantitative value image (a parameter image). When an imaging method for obtaining such a quantitative value image of the various types of parameters is implemented, it is possible to use any of various types of readout sequences, and the type of readout sequence to be used and the imaging conditions are determined on the basis of characteristics such as the SN ratio, distortions, time, and the like.

As explained above, MRI apparatuses are capable of taking images of patients by using the various types of imaging methods. When implementing each of the imaging methods, different types of readout sequences and imaging processes are selectively used in accordance with the site serving as the imaged target and the imaging purpose.

For example, when the ASL method described above is implemented, as a readout sequence (an imaging sequence) for acquiring echo signals, an FE (GRE) based readout sequence such as FE (GRE), SSFP, or FE-EPI can be used. Further, an SE-based readout sequence such as FSE or SE-EPI can also be used. In addition, as a method for filling the k-space, it is possible to use any of various methods including Cartesian methods and non-Cartesian methods (spiral, radial, etc.). Among these methods, there is no single almighty method that is optimal for all the target sites (target organs) and all the purposes of use. Thus, users selectively use various methods as appropriate, depending on whether the procedure is MRA or MRP and depending on the organ serving as the imaged target.

In this situation, as described above, the FE (GRE) based pulse sequence has a higher SN ratio but is less resistant to non-uniformity of the magnetic field than the SE-based pulse sequence. Further, among FE-based pulse sequence methods, the SSFP-based pulse sequence (which may also be called Fast Imaging with Steady-state Precession [FISP]) method has a higher SN ratio but is even less resistant to non-uniformity of the magnetic field than the FLASH-based pulse sequence. For this reason, when images of the main trunk of the brain are to be acquired by using the ASL-MRA method, the FE-based pulse sequence is mainly used because of the presence of the paranasal sinus and the temporal bone of the skull. In contrast, when images of an abdominal organ are acquired, the SSFP-based pulse sequence is often used. Further, as for the brain, when images of peripheral arteries in a parietal region are to be acquired, it is known that the SSFP-based pulse sequence, which has a higher SN ratio, is excellent, because non-uniformity of the magnetic field is not much of concern.

Further, when a Time-Resolve MRA (trMRA) method is used, the labeled blood is present in the major arteries when the TI is short and moves to peripheral arteries as the TI becomes longer. For this reason, it means that the FE (GRE) based pulse sequence is suitable when the TI is shorter and that the SSFP-based pulse sequence is suitable when the TI is longer. Further, when the 3D TOF-MRA method is used, the FE-based pulse sequence is suitable for the vicinity of the circle of Willis (Willis ring), whereas the SSFP-based pulse sequence is suitable for the parietal region.

As explained above, as for imaging methods implemented by MRI apparatuses, it is desirable to selectively use different types of readout sequences and imaging conditions depending on what is suitable for each position, in accordance with temporal positions during the imaging processes performed on the patient in a time series and spatial positions of the imaging region. Generally speaking, however, it is difficult for the operator to switch between different types of readout sequences and imaging conditions in accordance with the temporal positions and the spatial positions. Thus, a mechanism that exercises control on the apparatus side is in demand.

To cope with the problems of the conventional technique described above, the MRI apparatus 100 according to the first embodiment is configured to divide either a temporal range or a spatial range used when images of a patient are to be acquired, into at least two ranges. The MRI apparatus 100 is configured to perform a data acquiring process on a first range by using a first readout sequence and to perform a data acquiring process on a second range by using a second readout sequence that is different from the first readout sequence in terms of either the type of sequence or imaging conditions. Further, the MRI apparatus 100 is configured to combine an image generated from data acquired by using the first readout sequence with an image generated from data acquired by using the second readout sequence.

With this configuration, by arranging either the type or the imaging conditions of the first readout sequence to be suitable for performing the imaging process on the first range and arranging either the type or the imaging conditions of the second readout sequence to be suitable for performing the imaging process on the second range, it is possible to perform the imaging processes while using suitable readout sequences in accordance with the temporal positions or the spatial positions that are used when the images of the patient are acquired. In other words, by using the MRI apparatus 100 according to the first embodiment, it is possible to easily obtain images having high quality, by performing the imaging processes while using either the type or the imaging conditions of the readout sequence suitable for each position, in accordance with either the temporal positions or the spatial positions that are used when the images of the patient are acquired.

In the following sections, a detailed configuration of the MRI apparatus 100 according to the first embodiment and a flow in a process performed by the MRI apparatus 100 according to the first embodiment will be explained. In the first embodiment, an example will be explained in which images of blood vessels in the head of a patient are acquired by using a Single-Tag Multiple-TI (ST-MI) ASL method by which data acquiring processes are successively performed, by performing a data acquiring process every time a different one of a plurality of waiting periods has elapsed since an RF wave is applied once for the purpose of labeling fluid flowing into an imaging region of the patient. Further, in the first embodiment, an example will be explained in which a commonly-used FE-based pulse sequence (hereinafter, simply "FE-based pulse sequence") readout sequence will be used as the first readout sequence, whereas an SSFP-based readout sequence will be used as the second readout sequence.

Figure 7:
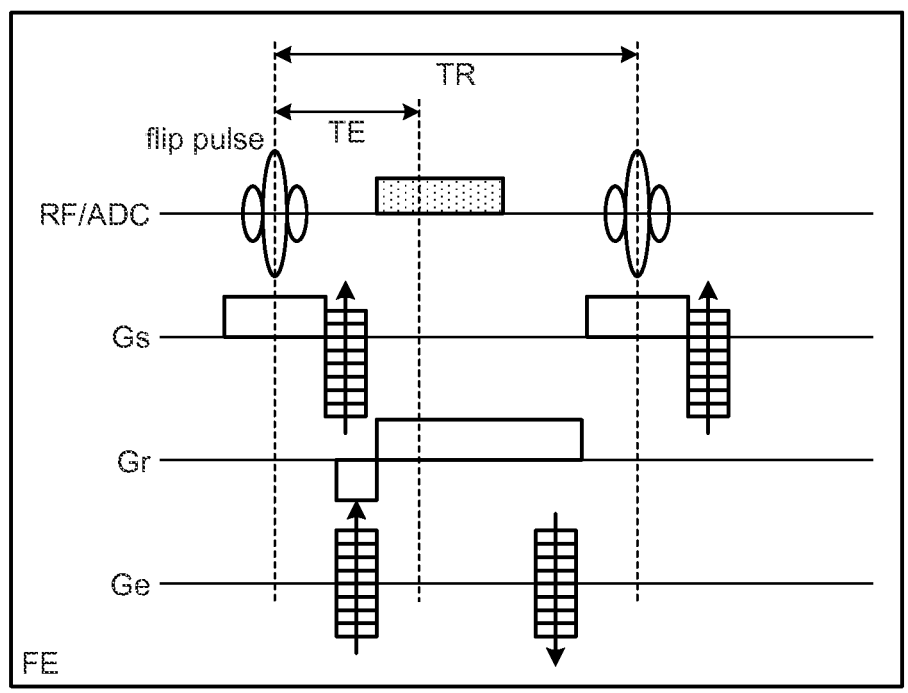
FIG. 7 is a chart of an example of an FE-based readout sequence according to the first embodiment.
Figure 8:
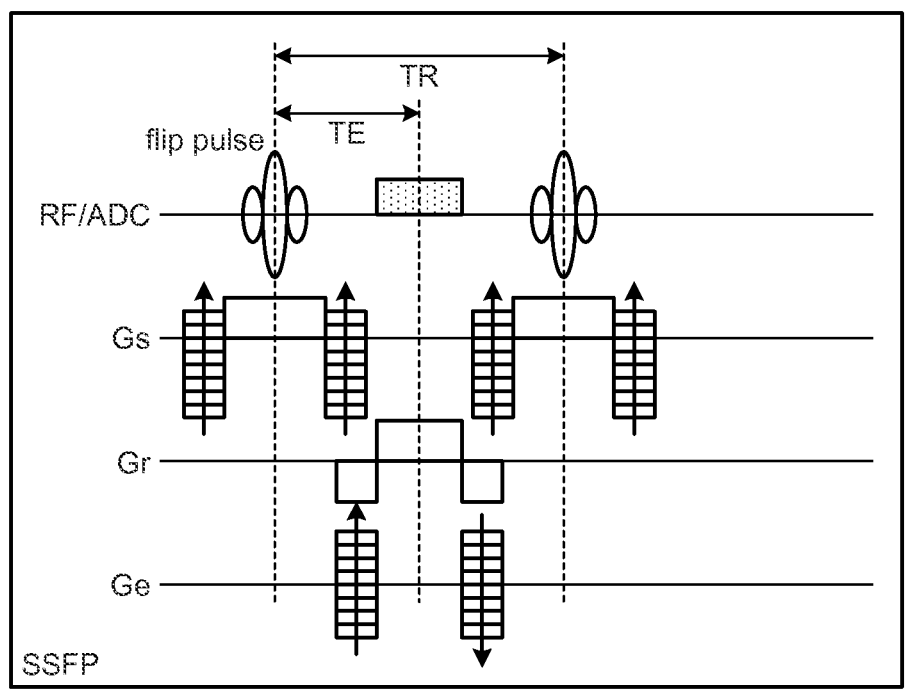
FIG. 8 is a chart of an example of an SSFP-based readout sequence according to the first embodiment.

FIG. 7 is a chart of an example of the FE-based readout sequence according to the first embodiment. FIG. 8 is a chart of an example of the SSFP-based readout sequence according to the first embodiment. Both of the readout sequences illustrated in FIGS. 7 and 8 are each a readout sequence for a 3D imaging process. More specifically, the FE-based readout sequence illustrated in FIG. 7 is configured to generate echo signals by inverting the read-out-purpose gradient magnetic field Gr and is further configured to apply a rewinding-purpose gradient magnetic field to the phase-encoding-purpose gradient magnetic field Ge for the purpose of cancelling the applied gradient magnetic field after the data acquiring process. The SSFP-based readout sequence illustrated in FIG. 8 is configured to apply, in the readout sequence illustrated in FIG. 7, a rewinding-purpose gradient magnetic field to each of all of the slice-selecting-purpose gradient magnetic field Gs, the phase-encoding-purpose gradient magnetic field Ge, and the read-out-purpose gradient magnetic field Gr, in such a manner that the integrated value of the gradient magnetic fields becomes zero within the repetition time TR.

In this situation, the SSFP-based readout sequence illustrated in FIG. 8 has a higher SN ratio per unit acquisition period but is less resistant to non-uniformity of the magnetic field than the FE-based readout sequence illustrated in FIG. 7, because the rewinding-purpose gradient magnetic field is applied in each of the directions of the three axes so as to adjust the integral value of the gradient magnetic fields. In contrast, the FE-based readout sequence illustrated in FIG. 7 is more resistant to non-uniformity of the magnetic field and has a higher spatial resolution, but has a lower SN ratio per unit acquisition period than the SSFP-based readout sequence illustrated in FIG. 8.

Accordingly, in the first embodiment, when images of blood vessels in the head of a patient are to be acquired by using the ST-MI-ASL method, the MRI apparatus 100 is configured to divide a temporal range used when the images are acquired, into at least two ranges, on the basis of the waiting period from when the labeling-purpose RF wave is applied, to when the data acquiring process is performed. After that, of the two ranges resulting from the division, the MRI apparatus 100 performs a data acquiring process on the range having the shorter waiting period by using the FE-based readout sequence that is more resistant to non-uniformity of the magnetic field and performs a data acquiring process on the range having the longer waiting period by using the SSFP-based readout sequence that has a higher SN ratio.

Figure 9:
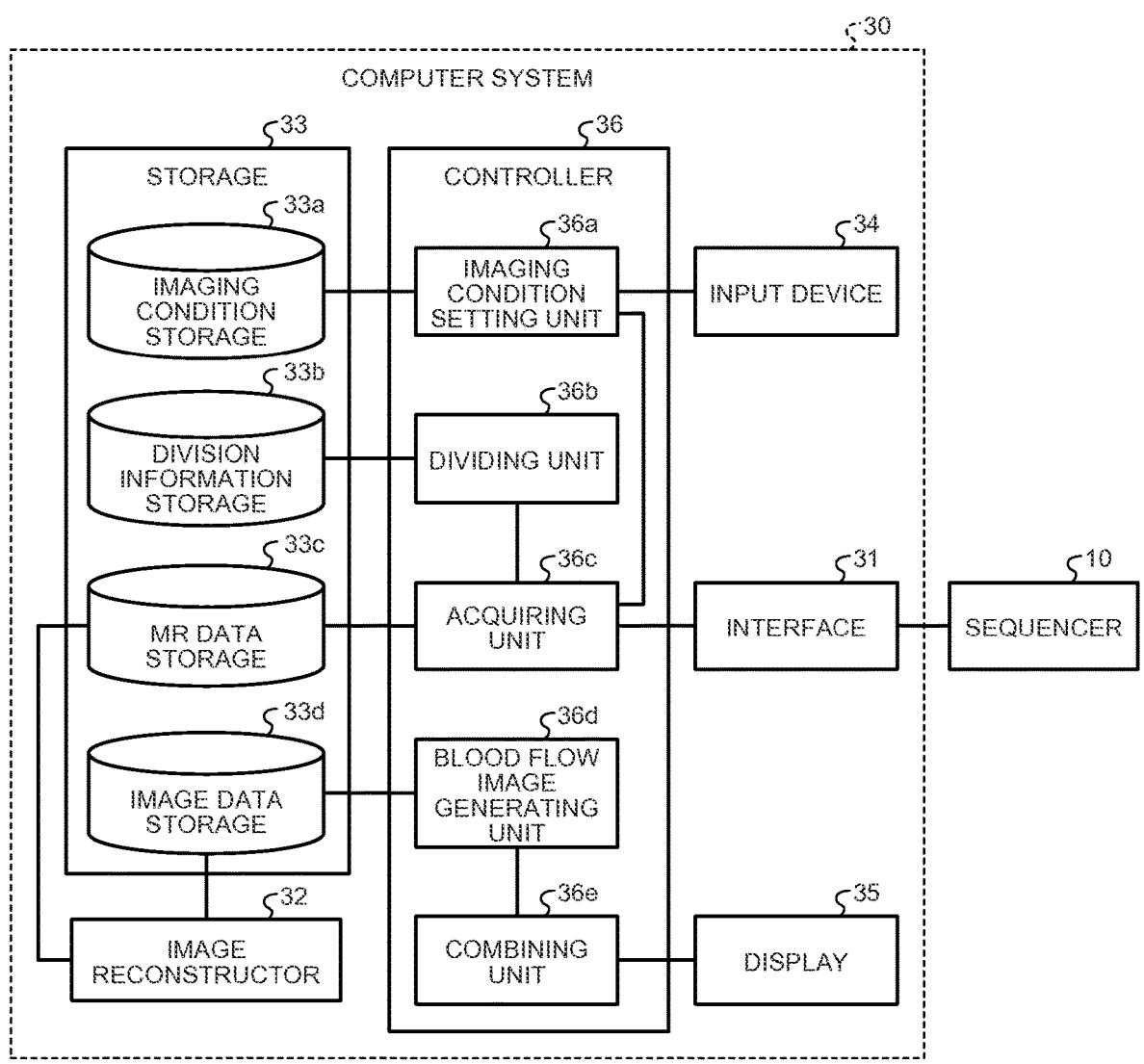
FIG. 9 is a diagram of an exemplary detailed configuration of the MRI apparatus according to the first embodiment.

FIG. 9 is a diagram of an exemplary detailed configuration of the MRI apparatus 100 according to the first embodiment. FIG. 9 illustrates the sequencer 10 and the computer system 30 illustrated in FIG. 1. Further, from among the functional units included in the computer system 30, FIG. 9 illustrates the interface 31, the image reconstructor 32, the storage 33, the input device 34, the display 35, and the controller 36.

As illustrated in FIG. 9, the storage 33 includes an imaging condition storage 33a, a division information storage 33b, an MR data storage 33c, and an image data storage 33d.

The imaging condition storage 33a is configured to store therein imaging conditions for each of different types of readout sequences used for taking images of the patient. In this situation, the imaging conditions represent parameter values of various types of imaging parameters required by the generation of the readout sequences. For example, the imaging conditions may include an acquisition matrix, a Number of Acquisitions (NAQ) value, a slab thickness, the number of slices in each slab, the number of shots, a SENSE factor, and the like. Further, the imaging conditions also include the type of sampling method such as PROPELLER, a radial-type, or the like. In the first embodiment, the imaging condition storage 33a stores therein at least imaging conditions related to the FE-based readout sequence and imaging conditions related to the SSFP-based readout sequence.

The division information storage 33b is configured to store therein information to be used as a reference for dividing either the temporal range or the spatial range used when the images of the patient are acquired. For example, the division information storage 33b stores therein anatomical information related to the site serving as an imaged target. In the first embodiment, when images of blood vessels in the head of the patient are acquired by using the ST-MI-ASL method, the division information storage 33b stores therein, as the information used for dividing a temporal range into a range in which the labeled blood flows through major arteries and a range in which the labeled blood flows through peripheral arteries, a waiting period until the labeled blood reaches the vicinity of a second branching point while a branching point where the Middle Cerebral Artery (MCA) branches to the left and the right is considered as a first branching point.

The information stored in the division information storage 33b does not necessarily have to be anatomical information. For example, the division information storage 33b may store therein such a waiting period among waiting periods used as a reference in imaging processes performed in the past that is judged by the operator to be most suitable. In other words, the division information storage 33b may store therein empirical values of the operator related to the waiting periods.

The MR data storage 33c is configured to store therein the MR data received from the sequencer 10 via the interface 31. The image data storage 33d is configured to store therein images reconstructed from the MR data by the image reconstructor 32.

Further, the controller 36 includes an imaging condition setting unit 36a, a dividing unit 36b, an acquiring unit 36c, a blood flow image generating unit 36d, and a combining unit 36e.

The imaging condition setting unit 36a is configured to set imaging conditions for each of the different types of readout sequences used for taking the images of the patient. More specifically, the imaging condition setting unit 36a receives an input of parameter values of various types of imaging parameters from the operator via the input device 34 and further registers the received parameter values into the imaging condition storage 33a as the imaging conditions. In the first embodiment, the imaging condition setting unit 36a sets at least imaging conditions related to the FE-based readout sequence and imaging conditions related to the SSFP-based readout sequence.

The dividing unit 36b is configured to divide either the temporal range or the spatial range used when the images of the patient are acquired, into at least two ranges. More specifically, the dividing unit 36b divides either the temporal range or the spatial range, on the basis of the information stored in the division information storage 33b. In the first embodiment, when the images of the blood vessels in the head of the patient are to be acquired by using the ST-MI-ASL method, the dividing unit 36b divides the temporal range used when the images are acquired, into at least two ranges, on the basis of the waiting period from when the labeling-purpose RF wave is applied, to when the data acquiring process is performed.

For example, by setting at least one of a plurality of waiting periods as a threshold value, the dividing unit 36b divides the temporal range used when the images are acquired, into at least two ranges. More specifically, the dividing unit 36b sets such a waiting period among a plurality of waiting periods used in the ST-MI-ASL method that is equal to the waiting period stored in the division information storage 33b, as the threshold value. In the first embodiment, the dividing unit 36b divides the temporal range into the range in which the labeled blood flows through the major arteries and the range in which the labeled blood flows through the peripheral arteries, by setting the threshold value to be the waiting period until the labeled blood reaches the vicinity of the second branching point while the branching point where the MCA branches to the left and the right is considered as the first branching point.

Of the two or more ranges resulting from the dividing process performed by the dividing unit 36b, the acquiring unit 36c is configured to perform a data acquiring process on a first range by using a first readout sequence and to perform a data acquiring process on a second range by using a second readout sequence that is different from the first readout sequence in terms of either the type of readout sequence or the imaging conditions.

In the first embodiment, when the images of the blood vessels in the head of the patient are to be acquired by using the ST-MI-ASL method, the acquiring unit 36c performs, of the two ranges resulting from the division, the data acquiring process on the range having the shorter waiting period by using the FE-based readout sequence and the data acquiring process on the range having the longer waiting period by using the SSFP-based readout sequence. More specifically, the acquiring unit 36c generates FE-based sequence information and SSFP-based sequence information, on the basis of the imaging conditions stored in the imaging condition storage 33a. Further, the acquiring unit 36c transmits the generated pieces of sequence information to the sequencer 10 and controls the sequencer 10 so as to implement the ST-MI-ASL method by using the pieces of sequence information.

Figure 10:
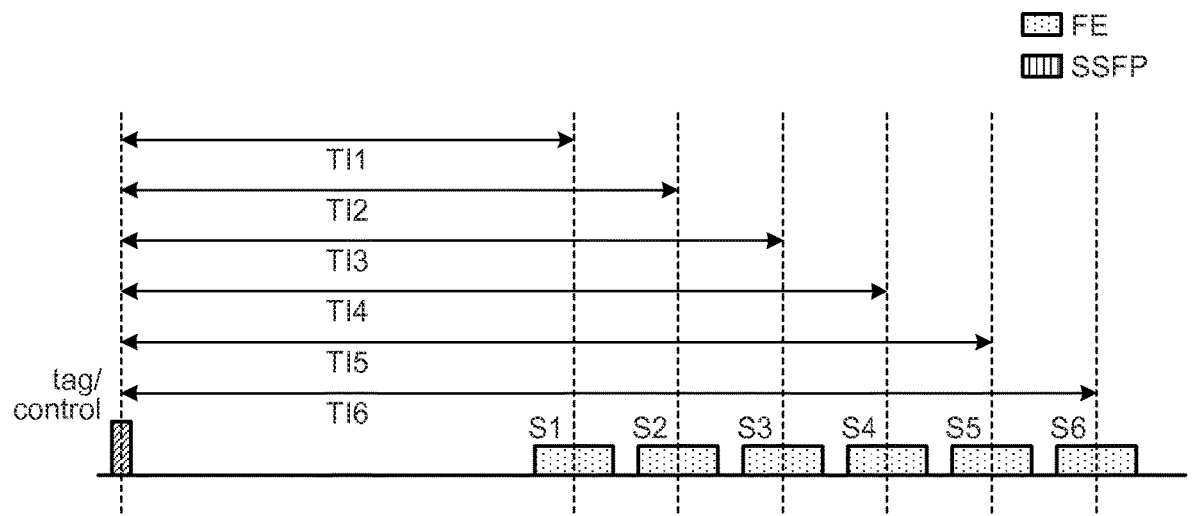
FIG. 10 is a chart of data acquiring processes according to a conventional Single-Tag Multiple-TI Arterial Spin Labeling (ST-MI-ASL) method.
Figure 11:
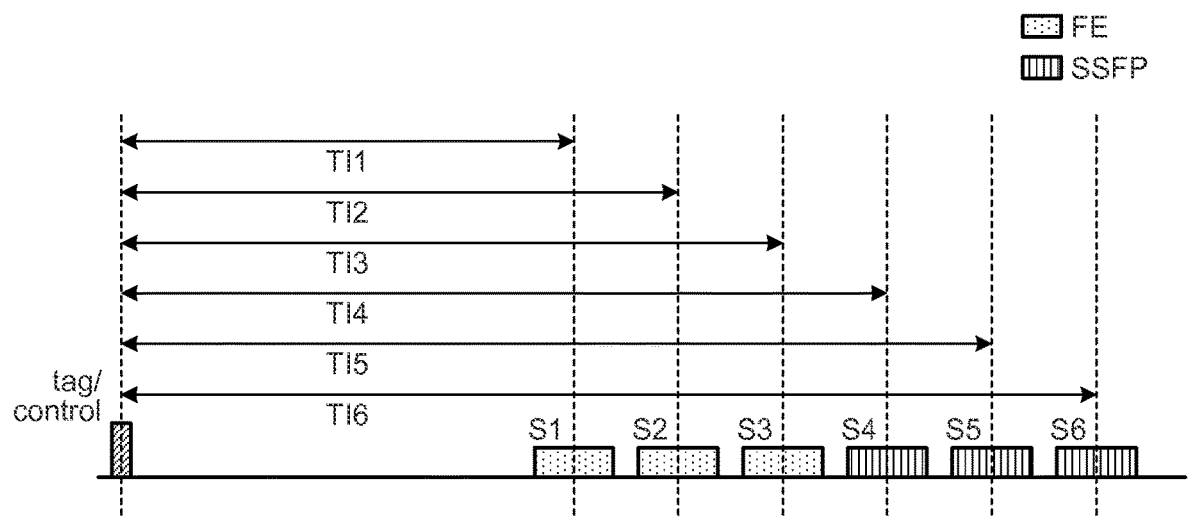
FIG. 11 is a chart of an ST-MI-ASL method implemented by an acquiring unit according to the first embodiment.

FIG. 10 is a chart of data acquiring processes according to a conventional ST-MI-ASL method. Further, FIG. 11 is a chart of an ST-MI-ASL method implemented by the acquiring unit 36c according to the first embodiment. As illustrated in FIG. 10, according to the conventional ST-MI-ASL method, the data acquiring processes are performed (steps S1 to S6) by using the readout sequences of mutually the same type (e.g., the FE-based readout sequences) in correspondence with a plurality of waiting periods TI1 to TI6.

In contrast, according to the first embodiment, the acquiring unit 36c switches between the readout sequences to be used for performing the data acquiring processes, on the basis of the waiting period threshold value set by the dividing unit 36b. For example, when the waiting period threshold value is TI3, the acquiring unit 36c controls the sequencer 10, as illustrated in FIG. 11, so as to perform a data acquiring process by using the FE-based readout sequence if the waiting period is equal to or shorter than TI3 and performs a data acquiring process by using the SSFP-based readout sequence if the waiting period exceeds TI3.

In this situation, in the first embodiment, the dividing unit 36b sets the threshold value to be the waiting period until the labeled blood reaches the vicinity of the second branching point while the branching point where the Middle Cerebral Artery (MCA) branches to the left and the right is considered as the first branching point. With this arrangement, in the first embodiment, the data acquiring process is performed on the range in which the labeled blood flows through the major arteries by using the FE-based readout sequence, whereas the data acquiring process is performed on the range in which the labeled blood flows through the peripheral arteries by using the SSFP-based readout sequence.

In this situation, for both of the data acquiring processes performed by using the FE-based readout sequence and the SSFP-based readout sequence, the acquiring unit 36c controls the sequencer 10 so as to acquire the data for a tag image and the data for a control image with each of the waiting periods. After that, when having received the MR data from the sequencer 10 via the interface 31, the acquiring unit 36c stores the received MR data into the MR data storage 33c. As a result, the image reconstructor 32 generates both the tag image and the control image from the MR data acquired by the sequencer 10, in correspondence with each of the plurality of waiting periods used in the ST-MI-ASL method.

Returning to the description of FIG. 9, the blood flow image generating unit 36d is configured to generate blood flow images each from the data acquired by using the first readout sequence and the data acquired by using the second readout sequence. In the first embodiment, the blood flow image generating unit 36d generates, as the blood flow image, a difference image between the tag image and the control image generated by the image reconstructor 32, for each of the plurality of waiting periods used in the ST-MI-ASL method. In other words, the blood flow image generating unit 36d generates the blood flow images for each of the waiting periods, with respect to the data acquired by using the FE-based readout sequence and the data acquired by using the SSFP-based readout sequence.

The combining unit 36e is configured to combine the image generated from the data acquired by using the first readout sequence with the image generated from the data acquired by using the second readout sequence. In the first embodiment, the combining unit 36e combines the blood flow images generated by the blood flow image generating unit 36d for each of the waiting periods, when the ST-MI-ASL method is implemented. In other words, the combining unit 36e combines the blood flow image generated from the data acquired by using the FE-based readout sequence with the blood flow image generated from the data acquired by using the SSFP-based readout sequence. After that, the combining unit 36e causes the display 35 to display the blood flow image resulting from the combining process.

In this situation, the combining unit 36e may combine the images together, after performing at least one correcting process selected from among a gain correction, a T1 relaxation correction, and an image interpolation, on one or both of the blood flow image generated from the data acquired by using the first readout sequence and the blood flow image generated from the data acquired by using the second readout sequence. In the first embodiment, the correcting process is performed on one or both of the blood flow image obtained by using the FE-based readout sequence and the blood flow image obtained by using the SSFP-based readout sequence.

Figure 12:
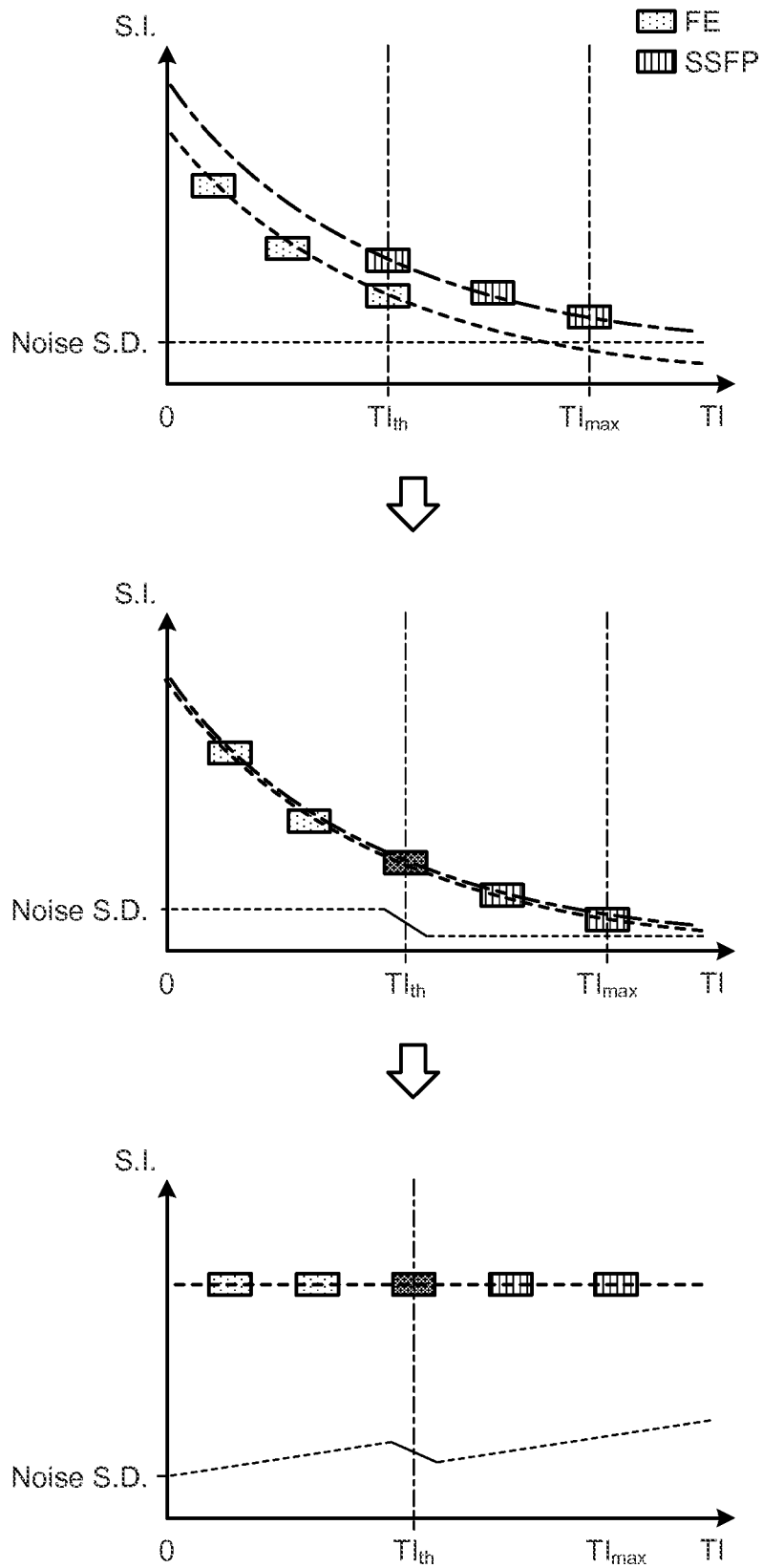
FIG. 12 presents charts for explaining an image correcting process performed by a combining unit according to the first embodiment.

FIG. 12 presents charts for explaining the image correcting process performed by the combining unit 36e according to the first embodiment. In each of the charts in the top, middle, and bottom sections of FIG. 12, the horizontal axis expresses the waiting period TI used in the ST-MI-ASL method, whereas the vertical axis expresses a Signal Intensity (S. I.) in the blood flow part of the blood flow image.

For example, as illustrated in the top section of FIG. 12, let us assume that data acquiring processes are performed on the range of $0<TI<TI_{th}$ by using the FE-based readout sequence, at $TI=TI_{th}$ by using both the FE-based readout sequence and the SSFP-based readout sequence, and on the range of $TI_{th}<TI<TI_{max}$ by using the SSFP-based readout sequence. In that situation, if the reception gains and the noise Standard Deviation (SD) values are arranged to be equal between the data acquiring processes performed by using the FE-based readout sequence and the SSFP-based readout sequence, the signal intensity in the blood flow part is larger in the blood flow image obtained by using the SSFP-based readout sequence than in the blood flow image obtained by using the FE-based readout sequence, in such a range where non-uniformity of the magnetic field is not of concern (i.e., in the range where TI is longer). In this situation, the noise SD value is a standard deviation of the signal intensity for each of the pixels contained in the image and serves as an index expressing characteristics of the noise.

Accordingly, the combining unit 36e performs the gain correction on one or both of the blood flow image obtained by using the FE-based readout sequence and the blood flow image obtained by using the SSFP-based readout sequence. For example, as illustrated in the middle section of FIG. 12, the combining unit 36e adjusts the reception gain for at least one of the data acquiring processes performed by using the mutually-different readout sequences, in such a manner that the signal intensities become equal between the data acquired by using the FE-based readout sequence and the data acquired by using the SSFP-based readout sequence when $TI=TI_{th}$ is satisfied.

In the example illustrated in the middle section of FIG. 12, a situation is explained where the reception gain for performing the data acquiring process by using the SSFP-based readout sequence is arranged to be equal to the reception gain for performing the data acquiring process by using the FE-based readout sequence. However, it is also acceptable, conversely, to arrange the reception gain for performing the data acquiring process by using the FE-based readout sequence to be equal to the reception gain for performing the data acquiring process by using the SSFP-based readout sequence. Alternatively, it is also acceptable to adjust both the reception gain for performing the data acquiring process by using the FE-based readout sequence and the reception gain for performing the data acquiring process by using the SSFP-based readout sequence.

Further, in the example illustrated in FIG. 12, at $TI=TI_{th}$, the data acquiring process is performed by using both the FE-based readout sequence and the SSFP-based readout sequence. However, it is not necessary to perform the mutually-different data acquiring processes in duplicate, for the same TI. In that situation, for example, the combining unit 36e adjusts the reception gain for at least one of the data acquiring processes performed by using the mutually-different readout sequences, in such a manner that the signal intensities become equal between the data corresponding to the last TI acquired by using the FE-based readout sequence and the data corresponding to the first TI acquired by using the SSFP-based readout sequence.

Further, the combining unit 36e may further perform the T1 relaxation correction after performing the gain correction described above. In that situation, for example, as illustrated in the bottom section of FIG. 12, in order to match the signal intensity in the blood flow part of the blood flow image obtained by using the FE-based readout sequence while TI=0 is satisfied, the combining unit 36e corrects the signal intensities in the blood flow parts of the blood flow images obtained in correspondence with the other TIs. For example, when the T1 value of the blood is expressed as T1b, the combining unit 36e corrects the signal intensities in the blood flow images by multiplying each of the signal values of the blood flow images obtained with the mutually-different TIs by {1/exp(−TI/T1b)}. For example, it is desirable to perform the T1 relaxation correction in the manner described above when the blood flow amount is quantified while implementing the ASL-MRP method.

Further, the combining unit 36e may further perform the image interpolation, after performing the gain correction described above. For example, with respect to the blood flow images generated in correspondence with the mutually-different waiting periods TI, the combining unit 36e generates an image by performing a weighted interpolation by using two blood flow images corresponding to two consecutive TIs and interpolates the two blood flow images with the generated image.

As explained above, by performing the gain correction on one or both of the blood flow image obtained by using the FE-based readout sequence and the blood flow image obtained by using the SSFP-based readout sequence, it is possible to arrange the signal intensity of the blood flow image obtained by using one of the readout sequences to be equal to the signal intensity of the blood flow image obtained by using the other readout sequence. It is therefore possible to improve the continuity of the blood vessels rendered in the combined image. Further, by performing the T1 relaxation correction and the image interpolation in addition to the gain correction, it is possible to further improve the continuity of the blood vessels rendered in the combined image. It is not necessary to perform all of the correcting processes described above (i.e., the gain correction, the T1 relaxation correction, and the image interpolation). It is acceptable to perform only one or two of the correcting processes.

Figure 13:
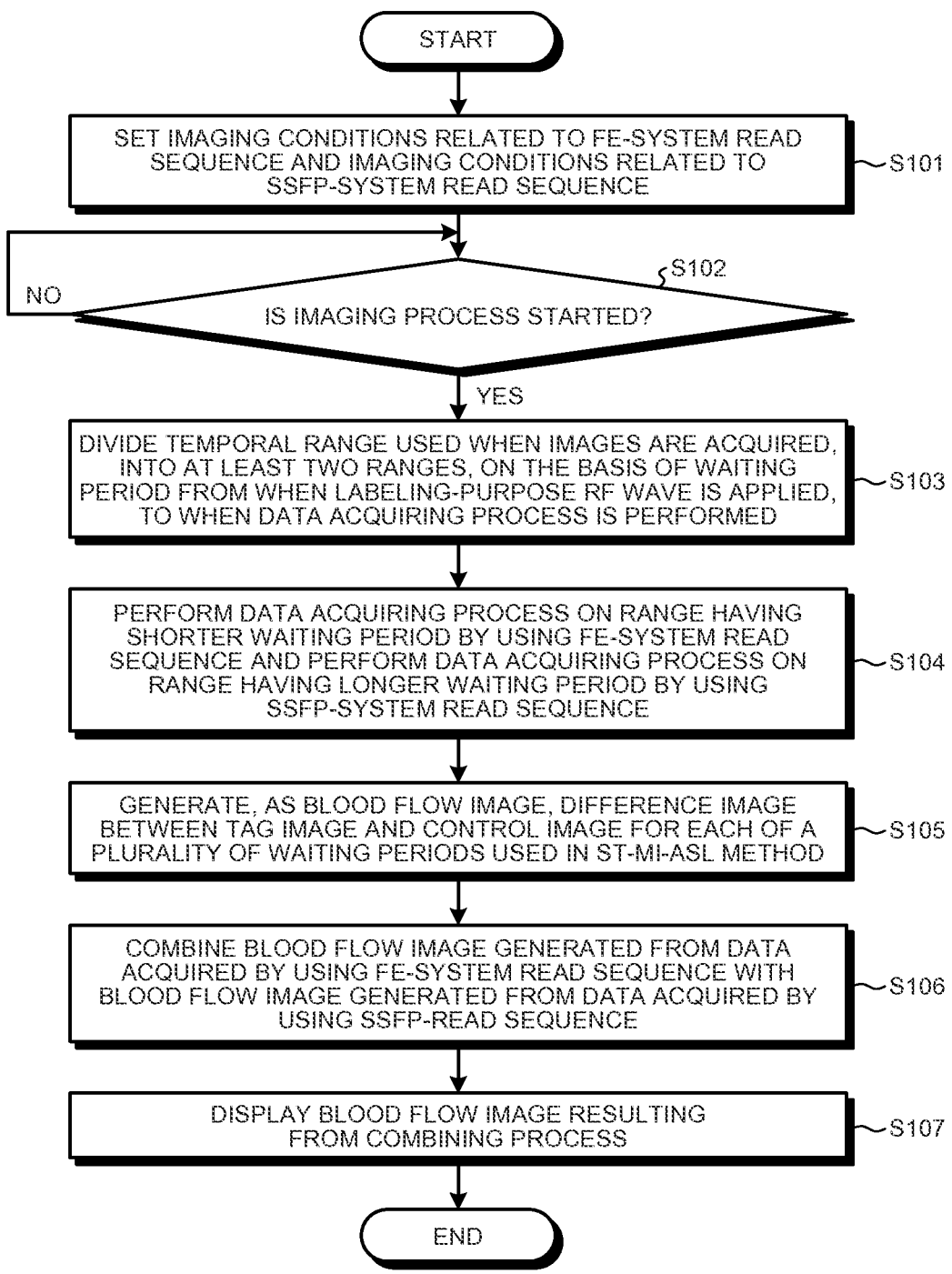
FIG. 13 is a flowchart of a flow in a process performed by the MRI apparatus according to the first embodiment.

FIG. 13 is a flowchart of a flow in a process performed by the MRI apparatus 100 according to the first embodiment. As illustrated in FIG. 13, in the MRI apparatus 100, the imaging condition setting unit 36a sets imaging conditions for each of the different types of readout sequences used for taking images of the patient. In the first embodiment, the imaging condition setting unit 36a sets at least imaging conditions related to the FE-based readout sequence and imaging conditions related to the SSFP-based readout sequence (step S101).

After that, when having received an instruction to start an imaging process from the operator (step S102: Yes), the dividing unit 36b divides either the temporal range or the spatial range used when the images of the patient are acquired, into at least two ranges. In the first embodiment, when images of blood vessels in the head of the patient are to be acquired by using the ST-MI-ASL method, the dividing unit 36b divides the temporal range used when the images are acquired, into at least two ranges, on the basis of the waiting period from when the labeling-purpose RF wave is applied, to when the data acquiring process is performed (step S103).

Subsequently, of the two or more ranges resulting from the dividing process performed by the dividing unit 36b, the acquiring unit 36c performs a data acquiring process on the first range by using the first readout sequence and performs a data acquiring process on the second range by using the second readout sequence that is different from the first readout sequence in terms of either the type of sequence or imaging conditions. In the first embodiment, of the two ranges resulting from the dividing process performed by the dividing unit 36b, the acquiring unit 36c performs a data acquiring process on the range having the shorter waiting period by using the FE-based readout sequence and performs a data acquiring process on the range having the longer waiting period by using the SSFP-based readout sequence (step S104).

The blood flow image generating unit 36d generates blood flow images each from the data acquired by using the first readout sequence and from the data acquired by using the second readout sequence. In the first embodiment, the blood flow image generating unit 36d generates, as the blood flow image, a difference image between the tag image and the control image generated by the image reconstructor 32, for each of the plurality of waiting periods used in the ST-MI-ASL method (step S105).

The combining unit 36e combines the image generated from the data acquired by using the first readout sequence with the image generated from the data acquired by using the second readout sequence. In the first embodiment, the combining unit 36e combines the blood flow image generated from the data acquired by using the FE-based readout sequence with the blood flow image generated from the data acquired by using the SSFP-based readout sequence (step S106). After that, the combining unit 36e causes the display 35 to display the blood flow image resulting from the combining process (step S107).

As explained above, the MRI apparatus 100 according to the first embodiment is configured, when the images of the blood vessels in the head of the patient are to be acquired by using the ST-MI-ASL method, to divide the temporal range used when the images are acquired, into at least two ranges, to perform the data acquiring process on the range having the shorter waiting period by using the FE-based readout sequence that is more resistant to non-uniformity of the magnetic field and has a higher spatial resolution, and to perform the data acquiring process on the range having the longer waiting period by using the SSFP-based readout sequence that has a higher SN ratio. It is therefore possible to obtain an image that renders both the major arteries and the peripheral arteries with a high level of precision. Consequently, by using the MRI apparatus 100 according to the first embodiment, it is possible to obtain images having higher quality in accordance with the site serving as the imaged target and the imaging purpose.

The first embodiment is explained by using the example in which the images of the patient are acquired by using the ST-MI-ASL method; however, possible imaging methods are not limited to this example. For example, the first embodiment is similarly applicable to a situation where a Single-Tag Single-TI ASL (ST-SI-ASL) method is used. The ST-SI-ASL method is an imaging method by which a pattern is formed where a data acquiring process is performed after a predetermined waiting period has elapsed since an RF wave is applied once for the purpose of labeling the fluid flowing into an imaging region of the patient, and the pattern is implemented multiple times while varying the waiting period.

When images of the patient are to be acquired by using the ST-SI-ASL method described above, for example, the dividing unit 36b divides, in the same manner as in the example using the ST-MI-ASL method, the temporal range used when the images are acquired, into at least two ranges, on the basis of the waiting period from when the labeling-purpose RF wave is applied, to when the data acquiring process is performed. After that, of the two or more ranges resulting from the dividing process performed by the dividing unit 36b, the acquiring unit 36c performs a data acquiring process on a first range by using a first readout sequence and performs a data acquiring process on a second range by using a second readout sequence that is different from the first readout sequence in terms of either the type of sequence or imaging conditions. For example, in the same manner as in the example using the ST-MI-ASL method, of the two ranges resulting from the division, the acquiring unit 36c performs the acquiring process on the range having the shorter waiting period by using the FE-based readout sequence and performs the data acquiring process on the range having the longer waiting period by using the SSFP-based readout sequence.

Further, if it is difficult to sample the data in the entire k-space by applying the RF-wave once, it is also acceptable to divide the k-space into a plurality of regions and to perform a data acquiring process by applying a labeling-purpose RF wave to each of the regions resulting from the division (hereinafter, "sectional regions"). In that situation, the data acquiring process is repeatedly performed by using the same waiting period until the data acquiring process has been performed on all of the sectional regions. When the data acquiring process has been performed on all of the sectional regions, a data acquiring process is then performed on the next k-space by using a different waiting period. In that situation also, the dividing unit 36b similarly divides the temporal range used when the images are acquired, into at least two ranges, on the basis of the waiting periods. Further, the acquiring unit 36c performs a data acquiring process on a first range by using a first readout sequence and performs a data acquiring process on a second range by using the second readout sequence that is different from the first readout sequence in terms of the type of sequence or imaging conditions.

Further, in the first embodiment, the example is explained in which the acquiring unit 36c changes the readout sequence used for performing the data acquiring process, on the basis of the threshold value for the waiting periods that is set by the dividing unit 36b. However, the control exercised over the readout sequences is not limited to this example. For instance, the acquiring unit 36c may change the readout sequence used for performing the data acquiring process, from the first readout sequence to the second readout sequence, when having detected that the labeled fluid has reached a predetermined position in the imaging region.

For example, when images of blood vessels in the head of a patient are acquired by using the ST-MI-ASL method, every time a blood flow image is generated by the blood flow image generating unit 36d, the acquiring unit 36c detects the position of the labeled blood in the generated blood flow image. After that, when detecting that the detected blood has reached the vicinity of the second branching point of the MCA, the acquiring unit 36c changes the readout sequence used for performing the data acquiring process from the FE-based readout sequence to the SSFP-based readout sequence.

Further, in the first embodiment, the example is explained in which, when the images of the blood vessels in the head of the patient are acquired by using the ST-MI-ASL method, the acquiring unit 36c changes the type of the readout sequence used for performing the data acquiring process from the FE-based pulse sequence to the SSFP-based pulse sequence. However, possible embodiments are not limited to this example. For instance, the acquiring unit 36c may change the imaging conditions of the readout sequence, instead of changing the type of readout sequence.

For example, when images of blood vessels in the head of a patient are to be acquired by using the ST-MI-ASL method, of the two ranges resulting from the dividing process performed by the dividing unit 36b, the acquiring unit 36c may, while using mutually the same type of readout sequence, perform a data acquiring process on the range having the shorter waiting period by using imaging conditions prioritizing the spatial resolution and perform a data acquiring process on the range having the longer waiting period by using imaging conditions prioritizing the SN ratio. In that situation, the imaging condition storage 33a stores therein the imaging conditions prioritizing the spatial resolution and the imaging conditions prioritizing the SN ratio, with respect to mutually the same type of readout sequence. The imaging conditions prioritizing the spatial resolution and the imaging conditions prioritizing the SN ratio are each set by adjusting, as appropriate, the acquisition matrix, the NAQ value, the slab thickness, the number of slices in each slab, the number of shots, and the like.

By changing the imaging conditions of the readout sequence as described above, it becomes also possible to switch the imaging method from the ASL-MRA method to the ASL-MRP method, in accordance with temporal positions during the imaging processes performed on the patient in a time series or spatial positions of the imaging region. When the ASL-MRA method is used, if the waiting period TI was prolonged while the spatial resolution keeps being prioritized, perfusion would not be rendered for being lower than the noise level due to the limit of the SN ratio. However, by changing the imaging method during the procedure so as to be in the mode prioritizing the SN ratio, it is possible to seamlessly render, in the images, the manner in which the labeled blood moves into the capillary bed as the waiting period TI is prolonged.

The acquiring unit 36c may also change both the type of pulse sequence and the imaging conditions, instead of changing one selected from between the type of pulse sequence and the imaging conditions used for performing the data acquiring processes. As a result, it is possible to acquire the data by using a more suitable method, in accordance with temporal positions during the imaging processes performed on the patient in a time series or spatial positions of the imaging region. It is therefore possible to obtain images having even higher quality.

Second Embodiment

Next, a second embodiment will be explained. In the second embodiment, an example will be explained in which data acquiring processes are performed by using two readout sequences of mutually-different types, on the entirety of either a temporal range or a spatial range used when images of a patient are acquired. The configuration of the MRI apparatus according to the second embodiment is basically the same as the configuration illustrated in FIGS. 1 and 9.

In the second embodiment, an example in which images of blood vessels in the head of the patient are to be acquired by using an ASL-MRA method that uses a multi-slab method, as well as an example in which images of blood vessels in the head of the patient are to be acquired by using an ASL-MRA method that uses the ST-MI-ASL method will be explained. In this situation, the multi-slab method is an imaging method by which an imaging region of the patient is divided into a plurality of sectional regions, so that a data acquiring process is performed on each of the plurality of sectional regions.

In the second embodiment, the acquiring unit 36c is configured to perform the data acquiring process on the entirety of either the temporal range or the spatial range used when the images of the patient are acquired, by using each of first and second readout sequences. Further, the combining unit 36e is configured to combine an image in a first range out of the image generated from the data acquired by using the first readout sequence with an image in a second range out of the image generated from the data acquired by using the second readout sequence.

Figure 14:
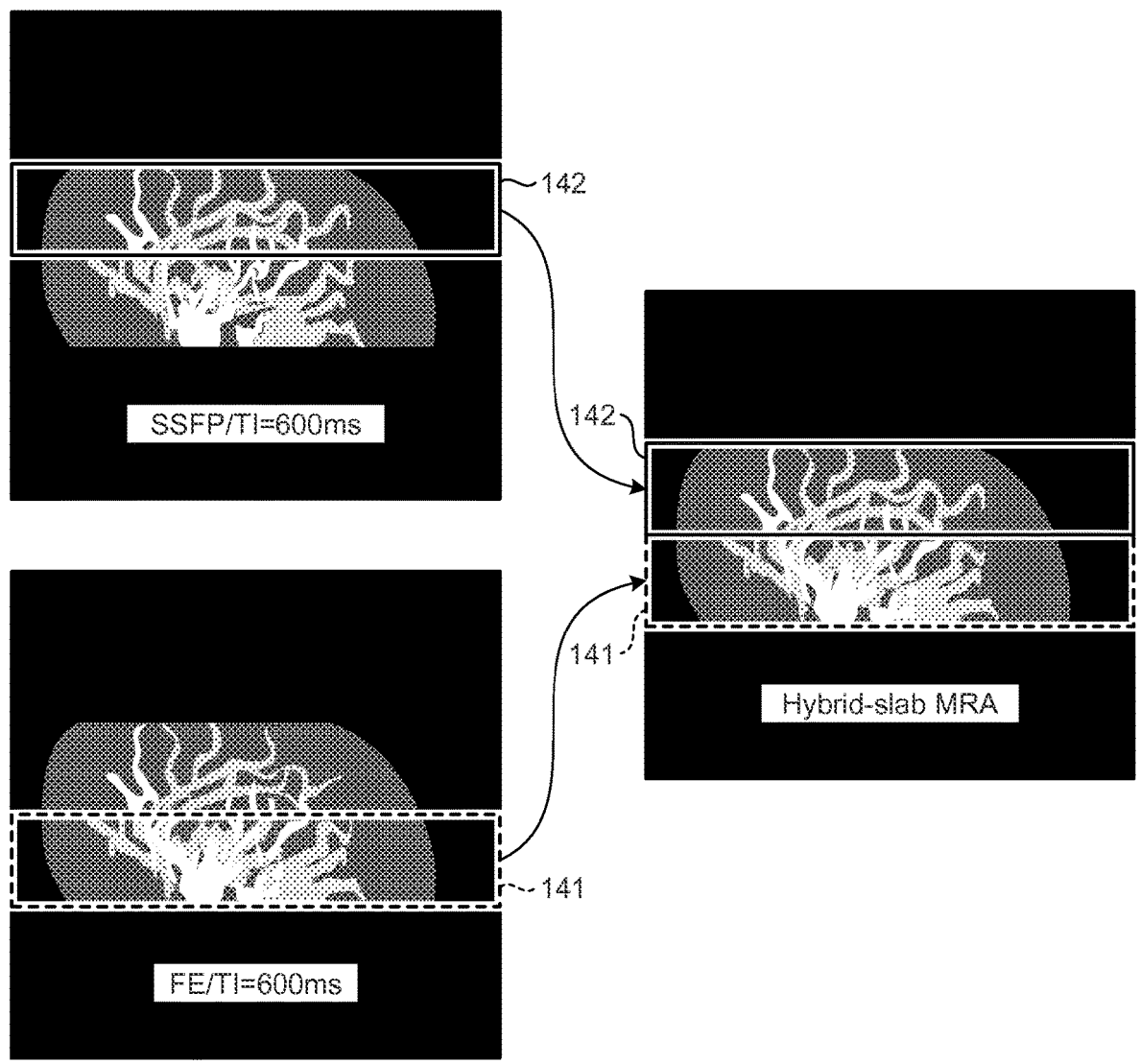
FIG. 14 is a drawing for explaining an Arterial Spin Labeling Magnetic Resonance Angiography (ASL-MRA) method implemented by an MRI apparatus according to a second embodiment.

FIG. 14 is a drawing for explaining the ASL-MRA method using the multi-slab method implemented by the MRI apparatus according to the second embodiment. FIG. 14 illustrates an example in which, when images of blood vessels in the head of the patient are acquired by using the ASL-MRA method using the multi-slab method, the data acquiring processes are performed by dividing the imaging region into two regions, namely, a sectional region 141 positioned on the major arteries side and a sectional region 142 positioned on the peripheral arteries side.

For example, as illustrated on the left side of FIG. 14, the acquiring unit 36c performs the data acquiring processes by using the FE-based readout sequence and the SSFP-based readout sequence for each of the waiting periods TI. After that, as illustrated on the right side of FIG. 14, the combining unit 36e combines an image of the sectional region 141 positioned on the major arteries side out of the blood flow image obtained by using the FE-based readout sequence with an image of the sectional region 142 positioned on the peripheral arteries side out of the blood flow image obtained by using the SSFP-based readout sequence. As a result, it is possible to obtain a blood flow image in which the region from the major arteries to the peripheral arteries is rendered in an excellent manner.

In this situation, for example, the combining unit 36e combines the blood flow images together, after arranging the weight on the signal values in the sectional region 141 positioned on the major arteries side to be larger than the weight on the signal values in the sectional region 142 positioned on the peripheral arteries side with respect to the blood flow image obtained by using the FE-based readout sequence, and also, arranging the weight on the signal values in the sectional region 142 positioned on the peripheral arteries side to be larger than the weight on the signal values in the sectional region 141 positioned on the major arteries side with respect to the blood flow image obtained by using the SSFP-based readout sequence.

In a specific example, for instance, the combining unit 36e combines the blood flow images together, after arranging the ratio between the weight on the signal values in the sectional region 141 and the weight on the signal values in the sectional region 142 to be 1:0 with respect to the blood flow image obtained by using the FE-based readout sequence, and also, arranging the ratio between the weight on the signal values in the sectional region 141 and the weight on the signal values in the sectional region 142 to be 0:1 with respect to the blood flow image obtained by using the SSFP-based readout sequence. In this situation, for example, the combining unit 36e combines the blood flow images together by performing either a weighted addition or a Maximum Intensity Projection (MIP) process.

Figure 15:
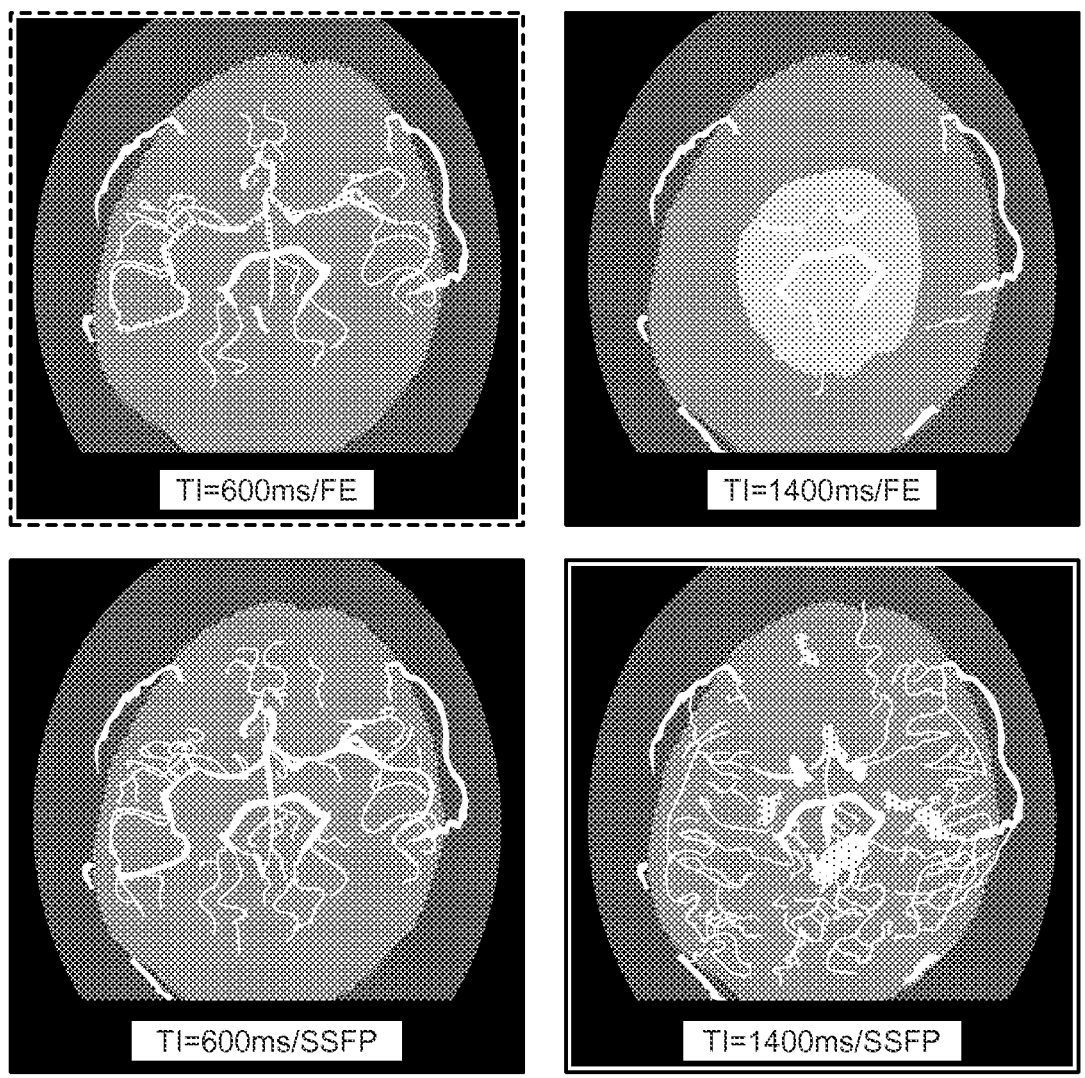
FIG. 15 is a drawing for explaining an ASL-MRA method using an ST-MI-ASL method implemented by the MRI apparatus according to the second embodiment.

FIG. 15 is a drawing for explaining the ASL-MRA method using the ST-MI-ASL method implemented by the MRI apparatus according to the second embodiment. FIG. 15 illustrates an example in which images of blood vessels in the head of a patient are acquired by using the ASL-MRA method using the ST-MI-ASL method. In FIG. 15, the image on the top left is an image obtained with TI=600 ms by using the FE-based readout sequence. The image on the top right is an image obtained with TI=1400 ms by using the FE-based readout sequence. Further, in FIG. 15, the image on the bottom left is an image obtained with TI=600 ms by using the SSFP-based readout sequence. The image on the bottom right is an image obtained with TI=1400 ms by using the SSFP-based readout sequence. In the examples illustrated in FIG. 15, it is assumed that the labeled blood reaches the major arteries when TI=600 ms is satisfied and reaches the peripheral arteries when TI=1400 ms is satisfied.

For example, as illustrated in FIG. 15, the acquiring unit 36c performs data acquiring processes by using the FE-based readout sequence and the SSFP-based readout sequence for each of the plurality of waiting periods TI. After that, the combining unit 36e generates dynamic images over the plurality of TIs, by using the blood flow image (the top left in FIG. 15) obtained by using the FE-based readout sequence with respect to TI=600 ms and using the blood flow image (the bottom right in FIG. 15) obtained by using the SSFP-based readout sequence with respect to TI=1400 ms. As a result, it is possible to obtain the dynamic images in which the region from the major arteries to the peripheral arteries is rendered in an excellent manner.

In this situation, for example, the combining unit 36e combines the blood flow images together for each of the TIs, after arranging the weight on the signal values in the blood flow image obtained by using the FE-based readout sequence to be larger than the weight on the signal values in the blood flow image obtained by using the SSFP-based readout sequence with respect to TI=600 ms, and also, arranging the weight on the signal values in the blood flow image obtained by using the SSFP-based readout sequence to be larger than the weight on the signal values in the blood flow image obtained by using the FE-based readout sequence with respect to TI=1400 ms.

In a specific example, for instance, the combining unit 36e combines the blood flow images together for each of the TIs, after arranging the ratio between the weight on the signal values in the blood flow image obtained by using the FE-based readout sequence and the weight on the signal values in the blood flow image obtained by using the SSFP-based readout sequence to be 1:0 with respect to TI=600 ms, and also, arranging the ratio between the weight on the signal values in the blood flow image obtained by using the FE-based readout sequence and the weight on the signal values in the blood flow image obtained by using the SSFP-based readout sequence to be 0:1 with respect to TI=1400 ms. In this situation, for example, the combining unit 36e combines the blood flow images together by performing either a weighted addition or a Maximum Intensity Projection (MIP) process.

Third Embodiment

Next, a third embodiment will be explained. In the third embodiment, an example will be explained in which images of blood vessels in the head of a patient are to be acquired by using a Pulsed Arterial Spin Labeling (PASL) method that uses a pulse wave as a labeling-purpose RF wave. The configuration of the MRI apparatus according to the third embodiment is basically the same as the configuration illustrated in FIGS. 1 and 9.

For example, when the images of the patient are to be acquired by using the PASL method, if the region to which the labeling-purpose RF wave is applied is set so as to be longitudinal along the direction in which the blood vessel extends, when the waiting period TI is prolonged, the labeled blood has flowed into the peripheral arteries, and also, has flowed into the major arteries. For this reason, when the waiting period TI is prolonged, if the SSFP-based readout sequence is used, a flow void may appear in a major artery part, or an artifact such as a ghost may appear in a part other than the blood vessels. Accordingly, when blood vessel images are combined together, it is desirable to ensure that no blood that has flowed into the major arteries is remaining in the blood vessel images corresponding to prolonged waiting periods TI.

For this reason, when images of a patient are to be acquired by using the PASL method, the MRI apparatus according to the third embodiment is configured to reduce the blood signals at a rear end of the blood labeled by the RF wave, by applying a saturation pulse to the tag region after a predetermined time period has elapsed since the labeling-purpose RF wave is applied to the tag region. The saturation pulse used in this situation may be called a Tag-End-Cut (TEC) pulse. By reducing the blood signals at the rear end portion of the labeled blood in this manner, it is possible to eliminate the blood that has flowed into the major arteries from the blood vessel images corresponding to the prolonged TI.

Figure 16:
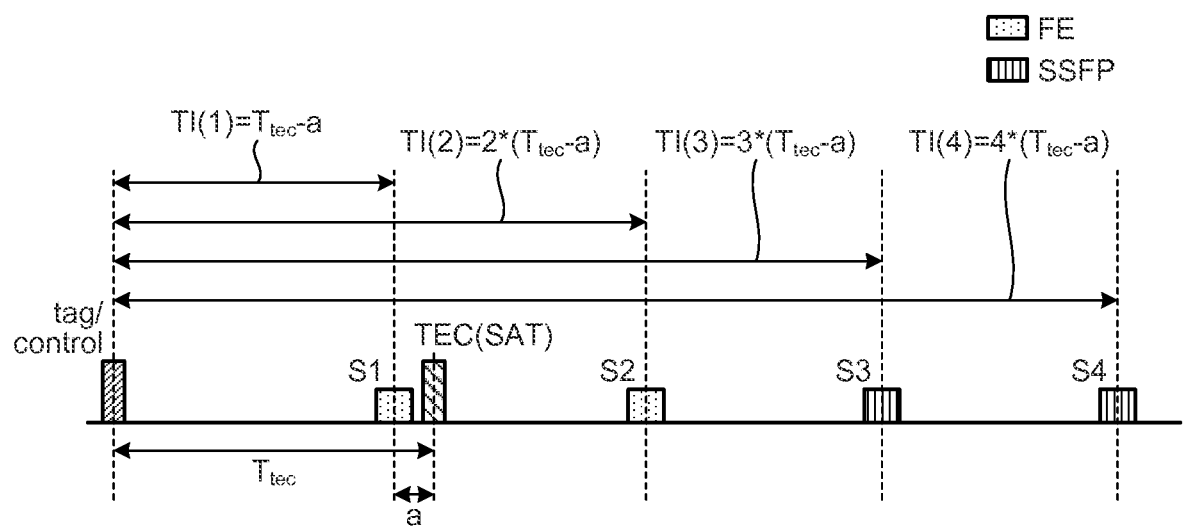
FIG. 16 is a first drawing for explaining a Pulsed Arterial Spin Labeling (PASL) method implemented by an MRI apparatus according to a third embodiment.
Figure 17:
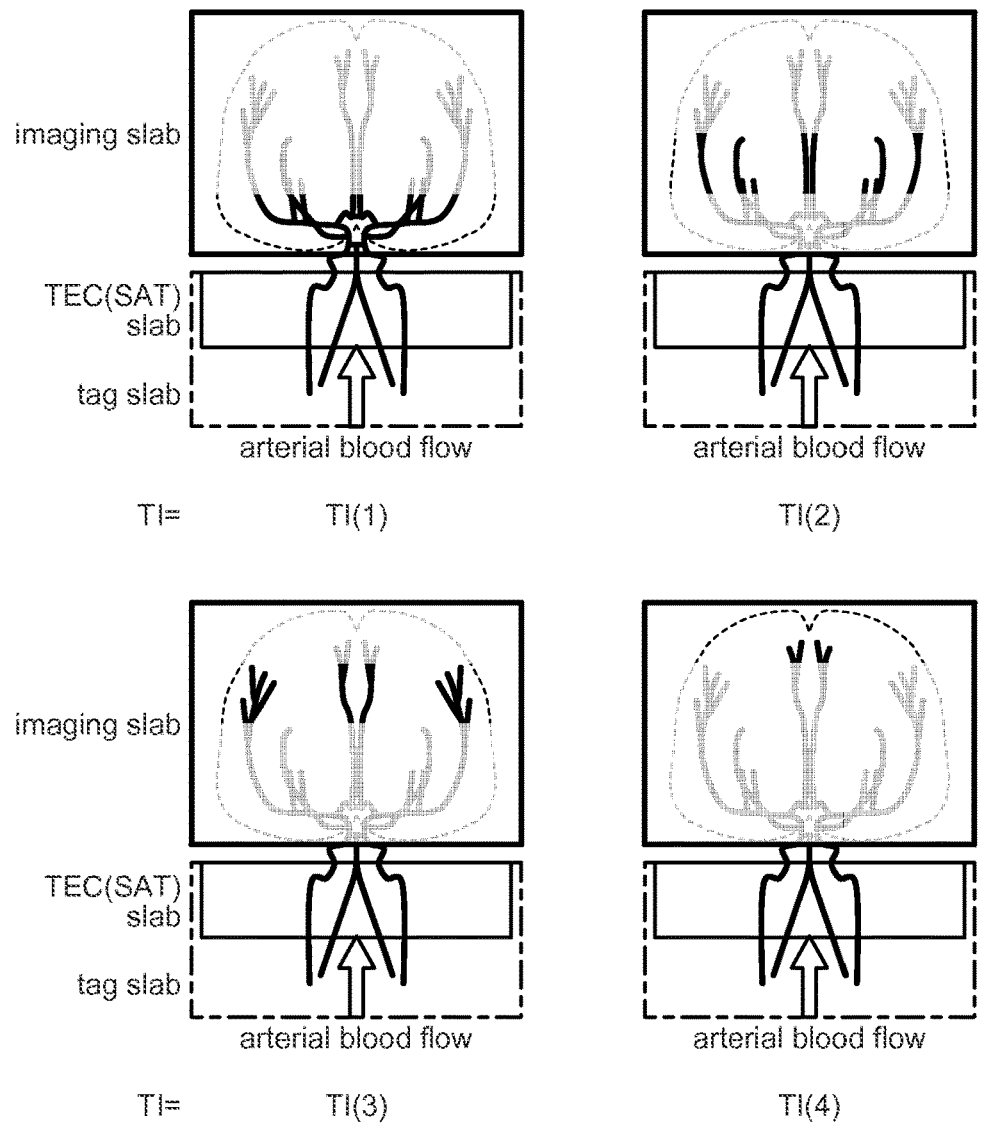
FIG. 17 is a second drawing for explaining the PASL method implemented by the MRI apparatus according to the third embodiment.
Figure 18:
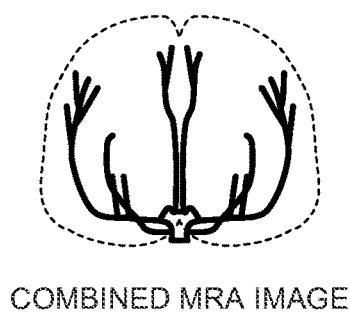
FIG. 18 is a third drawing for explaining the PASL method implemented by the MRI apparatus according to the third embodiment.

FIGS. 16 to 18 are drawings for explaining the PASL method implemented by the MRI apparatus according to the third embodiment. FIG. 16 illustrates a readout sequence of the PASL method according to the third embodiment. FIG. 17 illustrates a blood flow image obtained by implementing the PASL method according to the third embodiment. FIG. 18 illustrates a combined image obtained by implementing the PASL method according to the third embodiment.

In the readout sequence of the PASL method according to the third embodiment, a TEC pulse equivalent to the time span during which the labeling-purpose RF wave is applied is applied, after a predetermined time period $T_{tec}$ has elapsed since the labeling-purpose RF wave is applied. After that, the waiting period TI from when the labeling-purpose RF wave is applied, to when the data acquiring process is performed is prolonged in stages so as to be equal to integer multiples of $T_{tec}$. For example, the waiting period TI is varied so as to satisfy TI(1)=$T_{tec}$, TI(2)=2*$T_{tec}$, . . . , TI(n−1)=(n−1)*$T_{tec}$, and TI(n)=n*$T_{tec}$ (where n: a natural number), in ascending order of the length. In this situation, for example, as illustrated in FIG. 16, the increment by which TI is varied may be arranged to be smaller such as ($T_{tec}$−a) (where a: a constant; and a<$T_{tec}$).

As a result, for example, as illustrated in FIG. 17, it is possible to obtain blood flow images in which a bolus-like blood flow having a predetermined width advances in stages corresponding to the mutually-different waiting periods TI. Further, by combining these blood flow images together, for example, as illustrated in FIG. 18, it is possible to obtain a blood flow image of the entire head that includes the major arteries and the peripheral arteries. When the increment by which TI is varied is arranged to be ($T_{tec}$−a) as illustrated in FIG. 16, it is possible to arrange the boundaries of the labeled blood to overlap each other when combining the blood flow images together. As a result, it is possible to prevent the end parts of the blood vessels from having signalless portions at the boundaries of the blood flow images corresponding to mutually-different TIs. It is therefore possible to improve continuity of the blood vessels in the combined image.

Further, in the third embodiment, when the images of the patient are acquired by using the PASL method as described above, the acquiring unit 36c changes the readout sequence used for performing the data acquiring process, from the FE-based readout sequence to the SSFP-based readout sequence, while using a predetermined waiting period TI as a threshold value for the change. For example, as illustrated in FIG. 16, when using TI3 as the waiting period threshold value, the acquiring unit 36c controls the sequencer 10 so as to perform the data acquiring processes (steps S1 to S3) by using the FE-based readout sequence if the waiting period is equal to or shorter than TI3 and so as to perform the data acquiring processes (steps S4 to S6) by using the SSFP-based readout sequence if the waiting period exceeds TI3.

In the description above, the example using the PASL method is explained. However, the third embodiment is similarly applicable to situations where a Continuous Arterial Spin Labeling (CASL) method or a Pulsed Continuous Arterial Spin Labeling (PCASL) method is used. The CASL method is a method by which a continuous wave is used as the labeling-purpose RF wave. The PCASL method is a method by which a plurality of short pulse waves are used as the labeling-purpose RF wave, for the purpose of making the CASL method suitable for practical use.

According to the CASL method or the PCASL method, $T_{tec}$ corresponds to $T_{tag}$ expressing the application time period of the labeling-purpose RF wave. The waiting period from when the TEC pulse is applied, to when the data acquiring process is performed corresponds to a waiting period $T_{pld}$ (post labeling delay) from when the labeling-purpose RF wave is applied, to when the data acquiring process is performed. Accordingly, for example, when the CASL method or the PCASL method is used, $T_{pld}$ is prolonged at stages so as to be equal to integer multiples of $T_{tag}$. After that, in the same manner as in the example using the PASL method, the acquiring unit 36c changes the readout sequence used for performing the data acquiring process, from the FE-based readout sequence to the SSFP-based readout sequence, while using a predetermined waiting period TI as the threshold value for the change.

Further, the third embodiment is similarly applicable to a situation where the PASL method described above and the multi-slab method are used in combination. In that situation, the MRI apparatus implements an imaging method for taking images of the patient by using the imaging method by which an imaging region of the patient is divided into a plurality of sectional regions, so that a data acquiring process is performed every time a different one of a plurality of waiting periods respectively corresponding to the plurality of sectional regions has elapsed since an RF wave is applied for the purpose of labeling fluid flowing into the imaging region. After that, the dividing unit 36b divides a spatial range into at least two ranges, on the basis of the waiting period from when the labeling-purpose RF wave is applied, to when the data acquiring process is performed. Further, of the two ranges resulting from the division, the acquiring unit 36c performs a data acquiring process on the range having the shorter waiting period by using a first readout sequence and performs a data acquiring process on the range having the longer waiting period by using a second readout sequence. After that, the combining unit 36e generates an image of the imaging region by combining an image generated from the data acquired by using the first readout sequence with an image generated from the data acquired by using the second readout sequence. In other words, the combining unit 36e generates the image of the imaging region prior to the dividing process, by combining together the images of the plurality of sectional regions.

Figure 19:
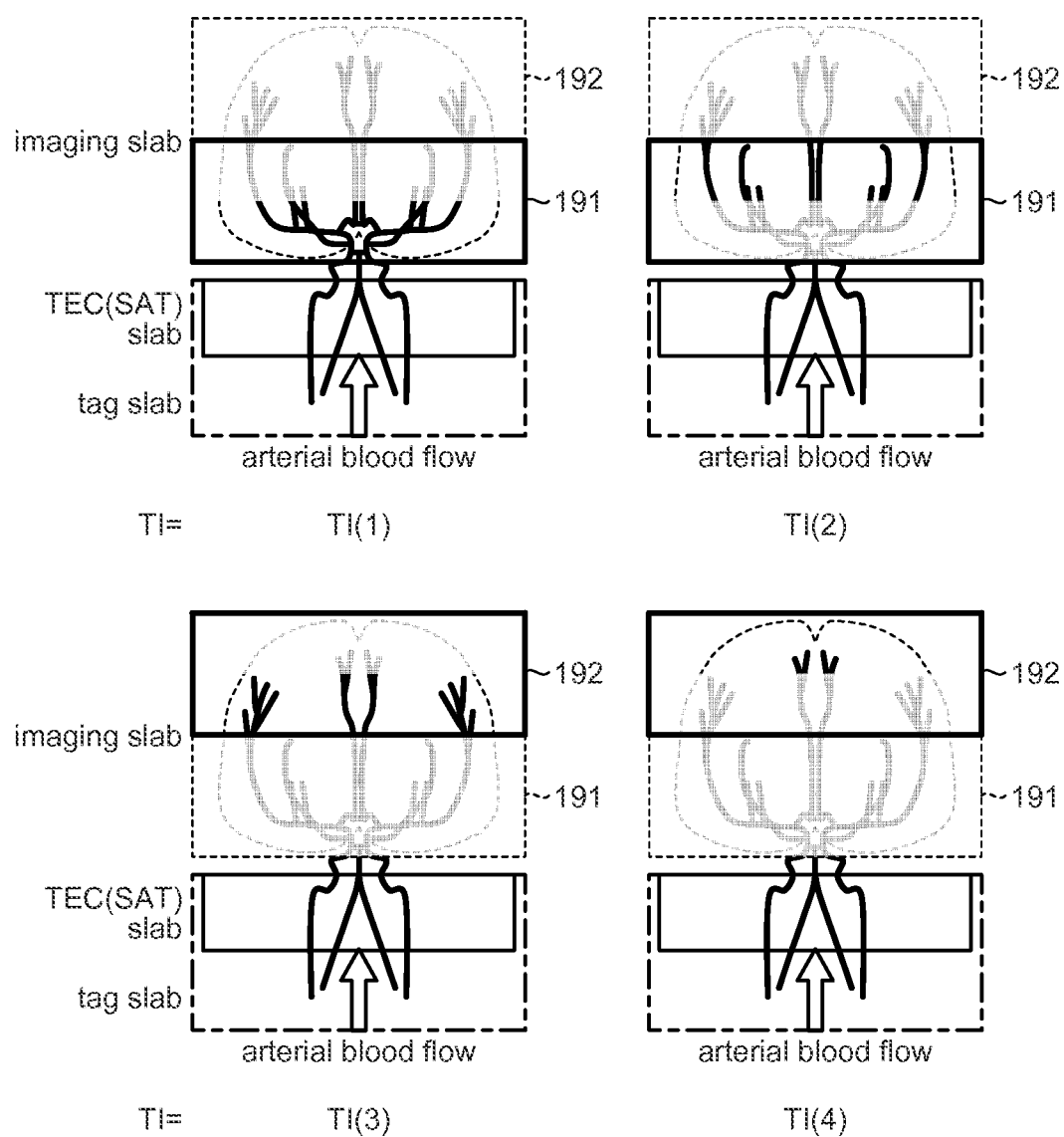
FIG. 19 is a drawing for explaining a PASL method using a multi-slab method implemented by the MRI apparatus according to the third embodiment.

FIG. 19 is a drawing for explaining the PASL method using the multi-slab method implemented by the MRI apparatus according to the third embodiment. FIG. 19 illustrates an example in which, when images of blood vessels in the head of a patient are to be acquired by implementing the PASL method using the multi-slab method, data acquiring processes are performed by dividing the imaging region into a sectional region 191 positioned on the major arteries side and a sectional region 192 positioned on the peripheral arteries side. In that situation, for example, the dividing unit 36b divides the imaging region that is set in the head of the patient into the sectional region 191 on the major arteries side corresponding to waiting periods TI(1) and TI(2) and the sectional region 192 on the periphery arteries side corresponding to waiting periods TI(3) and TI(4), on the basis of the waiting periods TI.

Further, in that situation, for example, the acquiring unit 36c controls the sequencer 10 so as to perform a data acquiring process by using the FE-based readout sequence with respect to waiting periods TI(1) and TI(2) and so as to perform a data acquiring process by using the SSFP-based readout sequence with respect to waiting periods TI(3) and TI(4). In that situation also, for example, as illustrate in FIG. 17, it is possible to obtain blood flow images in which a bolus-like blood flow having a predetermined width advances in stages corresponding to the mutually-different waiting periods TI. Further, by combining these blood flow images together, for example, as illustrated in FIG. 18, it is possible to obtain the blood flow image of the entire head that includes the major arteries and the peripheral arteries.

In the manner described above, by performing the data acquiring process on the sectional region positioned on the major arteries side corresponding to the shorter waiting period TI by using the FE-based readout sequence that is more resistant to non-uniformity of the magnetic field and has a higher spatial resolution and performing the data acquiring process on the sectional region positioned on the peripheral arteries side corresponding to the longer waiting period TI by using the SSFP-based readout sequence that has a higher SN ratio, it is possible to obtain the image in which both the major arteries and the peripheral arteries are rendered with a high level of precision.

In the description above, the example is explained in which the type of readout sequence is changed from the FE-based readout sequence to the SSFP-based readout sequence; however, it is also acceptable to change the conditions of the readout sequence. In that situation, for example, while using mutually the same type of readout sequences, the acquiring unit 36c performs a data acquiring process on the sectional region positioned on the major arteries side corresponding to the shorter waiting period TI by using imaging conditions prioritizing the spatial resolution and performs a data acquiring process on the sectional region positioned on the peripheral arteries side corresponding to the longer waiting period TI by using imaging conditions prioritizing the SN ratio.

Further, for example, the acquiring unit 36c may control the sequencer 10 so as to acquire data from the sectional region having the more blood vessel signals by using a single readout sequence and so as not to acquire data from the sectional region having the fewer blood signals. In that situation, it is desirable to set the widths of the sectional regions to be small in the direction in which the blood vessels extend, so that it is possible to finely divide the regions from which data is to be acquired and the regions from which no data is to be acquired.

Fourth Embodiment

Next, a fourth embodiment will be explained. In the fourth embodiment, an example will be explained in which images of a patient are to be acquired by using an imaging method by which a pattern is formed where a data acquiring process is performed after a predetermined waiting period has elapsed since an RF wave is applied for the purpose of labeling fluid flowing into an imaging region of the patient, and the pattern is implemented multiple times while varying the waiting period. The configuration of the MRI apparatus according to the fourth embodiment is basically the same as the configuration illustrated in FIGS. 1 and 9.

For instance, examples of such an imaging method include an HE-MT-PASL method, which is a Multi-Tag Pulsed Arterial Spin Labeling (MT-PASL) method that uses a Hadamard Encoding (HE) method. As for the HE method, for example, a method combined with the CASL method is proposed in Wells J A et al. In vivo hadamard encoded continuous arterial spin labeling (H-CASL). MRM 63:1111-1118 (2010). According to the HE-MT-PASL method, by acquiring data while efficiently arranging the RF waves for tag images and the RF waves for control images at predetermined time intervals and performing additions and subtractions on the acquired images, it is possible to obtain a plurality of ASL images corresponding to mutually-different waiting periods TI. By using this method, it is possible to further improve the SN ratio, compared to the ST-SI-ASL method or the ST-MI-ASL method.

Figure 20:
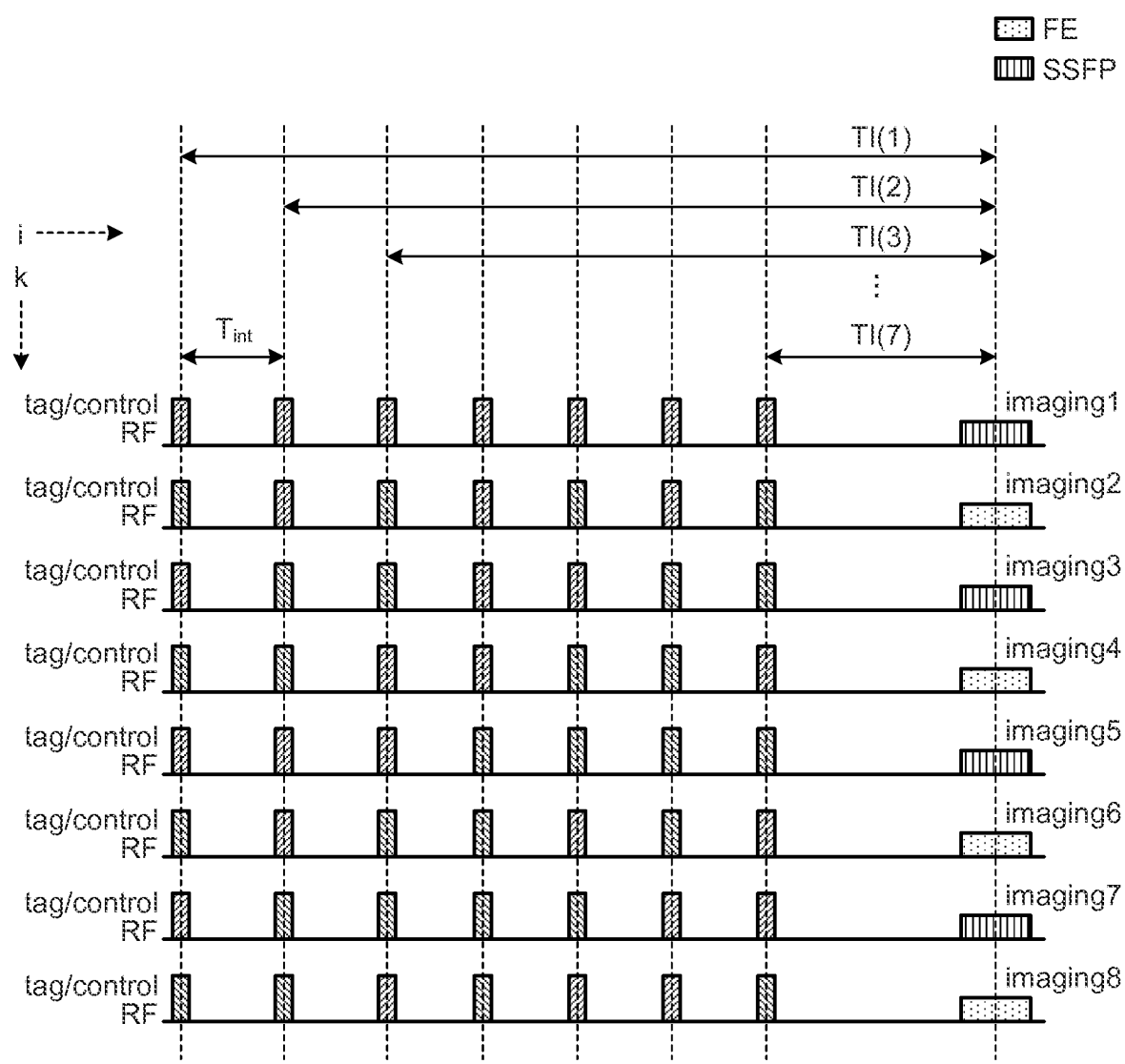
FIG. 20 is a drawing for explaining a Hadamard Encoding Multi-Tag Pulsed Arterial Spin Labeling (HE-MT-PASL) method implemented by an MRI apparatus according to a fourth embodiment.

FIG. 20 is a drawing for explaining the HE-MT-PASL method implemented by the MRI apparatus according to the fourth embodiment. When the HE-MT-PASL is used, for example, N expressing the number of mutually-different waiting periods TI in a set is arranged to satisfy N=2n−1 (where n: a natural number), i.e., 3, 7, 15, and so on. FIG. 20 illustrates an example in which the number of mutually-different waiting periods TI in a set satisfies N=7 (where n=2).

Among the plurality of RF waves (tag/control RF) illustrated in FIG. 20, the RF waves indicated with hatching with diagonal lines from the top right to the bottom left are the RF waves for the tag images, whereas the RF waves indicated with hatching with diagonal lines from the top left to the bottom right are the RF waves for the control images. As illustrated in FIG. 20, for example, when N=7 is satisfied, the set made up of eight types (N+1=8) of readout sequences that are for the two types of images and that have mutually-different order of RF waves is used. Further, the waiting period TI(i) of the readout sequences may be at arbitrary time intervals as long as the time intervals are equal among the patterns corresponding to k=1 to k=8.

In this situation, when a complex signal of the data acquired by using the patterns corresponding to k=1 to k=8 is expressed as Sk, it is possible to calculate a difference signal S{TI(i)} that is four times larger at each TI(i) (where i=1 to i=7) by using the following expression:

$$S\{TI(i)\}=4[S\{TI(i)\}-S\text{cont}\{TI(i)\}]$$

In other words, when i is set to satisfy i=1 to i=7, it is possible to calculate S{TI(1)} to S{TI(7)} by using the expressions shown below.

$$S\{TI(1)\}=S1-S2+S3-S4+S5-S6+S7-S8$$

$$S\{TI(2)\}=S1+S2-S3-S4+S5+S6-S7-S8$$

$$S\{TI(3)\}=S1-S2-S3+S4+S5-S6-S7+S8$$

$$S\{TI(4)\}=S1+S2+S3+S4-S5-S6-S7-S8$$

$$S\{TI(5)\}=S1-S2+S3-S4+S5-S6+S7-S8$$

$$S\{TI(6)\}=S1+S2-S3-S4-S5-S6+S7+S8$$

$$S\{TI(7)\}=S1-S2-S3+S4-S5+S6+S7-S8$$

In that situation, the SN ratio is twice as high because sqrt(4)=2, which corresponds to performing the addition four times while using the NAQ value, which is the difference of one time.

Further, when the repetition time for one time is expressed as $T_{repeat}$, the imaging period can be expressed as $(N+1)*T_{repeat}$ with respect to TIs of which the quantity in a set is equal to N. In contrast, when a data acquiring process is performed every time a labeling-purpose RF wave is applied once, the imaging period can be expressed as $2*(N+1)/2*N*T_{repeat}=N(N+1)*T_{repeat}$, with respect to TIs of which the quantity in a set is equal to N. Accordingly, the ratio of the imaging period of the HE-MT-SI method to the imaging period in the method by which the data acquiring process is performed every time the labeling-purpose RF wave is applied once can be calculated as $N+1/N(N+1)=1/N$. In other words, when N=7 is satisfied, it takes one-seventh of the time period to obtain the difference images that correspond to the mutually-different TIs and that have an SN ratio equal to the SN ratio in the example in which the data acquiring process is performed every time the labeling-purpose RF wave is applied once.

According to the ASL-MRP method, when a commonly-used ST-PASL method is used, an arithmetic mean is calculated a number of times in order to ensure a sufficient level of SN ratio. In contrast, when the HE-MT-PASL method described above is used, because it is possible to obtain the same data performing the acquiring process only once and because it is possible to obtain the image that is equivalent to performing the arithmetic mean with TIs varied at a number of stages, it is possible to effectively shorten the acquisition time period. In this situation, it is sufficient if the RF waves for the control images are applied only when the imaging is performed for an MRP purpose and MTC is of concern.

Accordingly, when the imaging is performed for the purpose of MRA of blood vessels and MTC is not of concern, it is acceptable to omit the RF waves for the control images.

Further, the HE-MT-PASL method described above has restrictions on the tag condition such as controlling the pulse intervals in accordance with the flow rate of the blood. Further, according to the HE method, if the flow rate of the blood fluctuates temporally, when the procedure is performed with a pulsatile flow, for example, unless the flow rates of the blood are equal between the times at which the RF waves are applied at mutually the same time, the fluid signals labeled at unnecessary timing may not be erased as intended in some situations, when additions and subtractions, especially subtractions, are performed on the images. The same applies to the situation where the HE method is combined with the PASL method and the situation where the HE method is combined with the CASL method. To cope with these situations, for example, the acquiring unit 36c may be configured to apply an initial RF wave by using, as a trigger signal, an R wave in a heartbeat gate signal detected by the ECG sensor 21 and the ECG device 22, so that the RF waves at mutually the same time are applied in mutually the same cardiac phase.

Further, in the fourth embodiment, when images of a patient are to be acquired by using the HE-MT-PASL method described above, the acquiring unit 36c performs data acquiring processes by using the FE-based readout sequence with respect to four of the eight types of patterns corresponding to k=1 to k=8 and performs data acquiring processes by using the SSFP-based readout sequence with respect to the other four types of patterns. In that situation, due to an average effect, it is possible to obtain images in which the images obtained by using the SSFP-based readout sequence are mixed with the images obtained by using the FE-based readout sequence.

For example, as illustrated in FIG. 20, when sequentially implementing the eight types of patterns, the acquiring unit 36c controls the sequencer 10 so as to alternately use the FE-based readout sequence and the SSFP readout sequence. In other words, the acquiring unit 36c exercises control so as to perform the data acquiring processes on the patterns corresponding to k=1, 3, 5, and 7 by using the SSFP-based readout sequence and so as to perform the data acquiring processes on the patterns corresponding to k=2, 4, 6, and 8 by using the FE-based readout sequence.

Alternatively, for example, the acquiring unit 36c may use the FE-based readout sequence with respect to patterns in which more RF waves for tag images are arranged on the side having the shorter TI and may use the FE-based readout sequence with respect to patterns in which more RF waves for tag images are arranged on the side having the longer TI.

As another example of the imaging method by which a pattern is formed where a data acquiring process is performed after a predetermined waiting period has elapsed since an RF wave is applied for the purpose of labeling fluid flowing into an imaging region of a patient, and the pattern is implemented multiple times while varying the waiting period, there is an imaging method by which the ST-MI-ASL method is implemented multiple times. To describe this imaging method, an example will be explained in which the pattern of the ST-MI-ASL method is implemented multiple times while varying the waiting period from when the labeling-purpose RF wave is applied, to when the initial data acquiring process is performed, and subsequently the acquired plurality of pieces of data are added together in groups each having mutually the same waiting period from the application of the RF wave to the data acquiring process.

Figure 21:
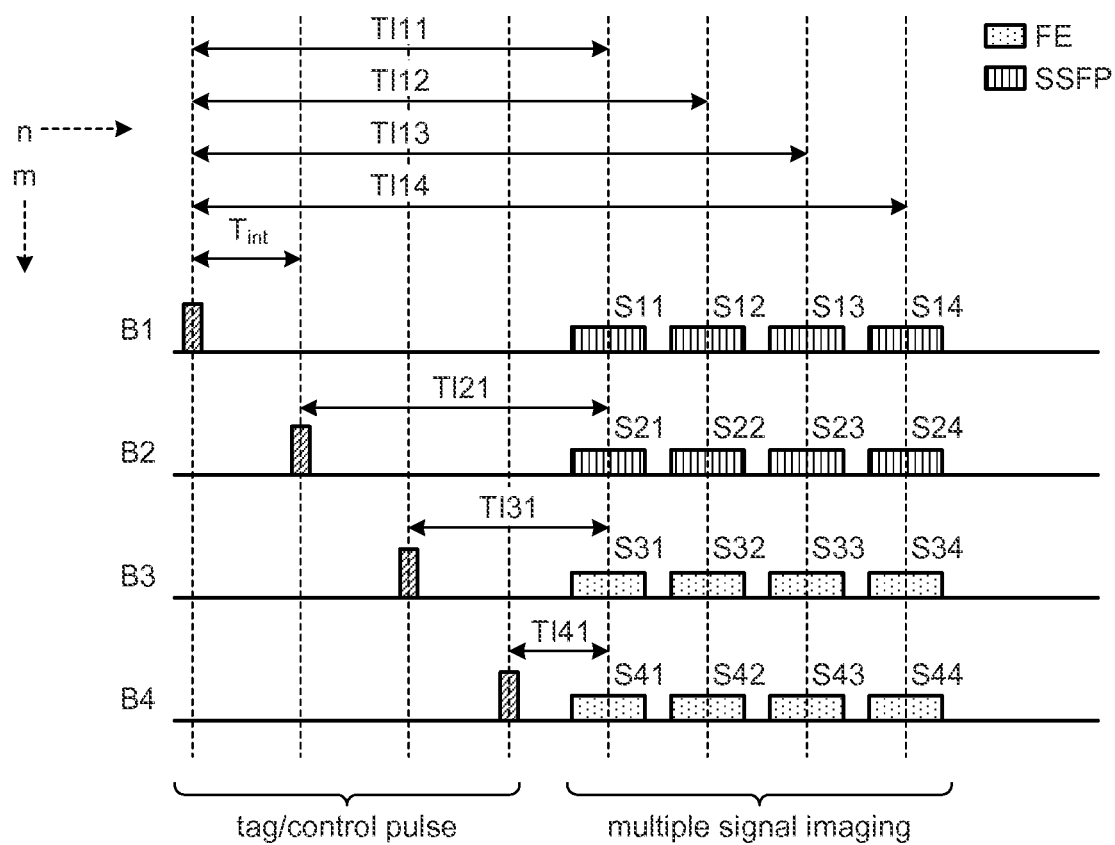
FIG. 21 is a first drawing for explaining an ST-MI-ASL method implemented by the MRI apparatus according to the fourth embodiment.
Figure 22:
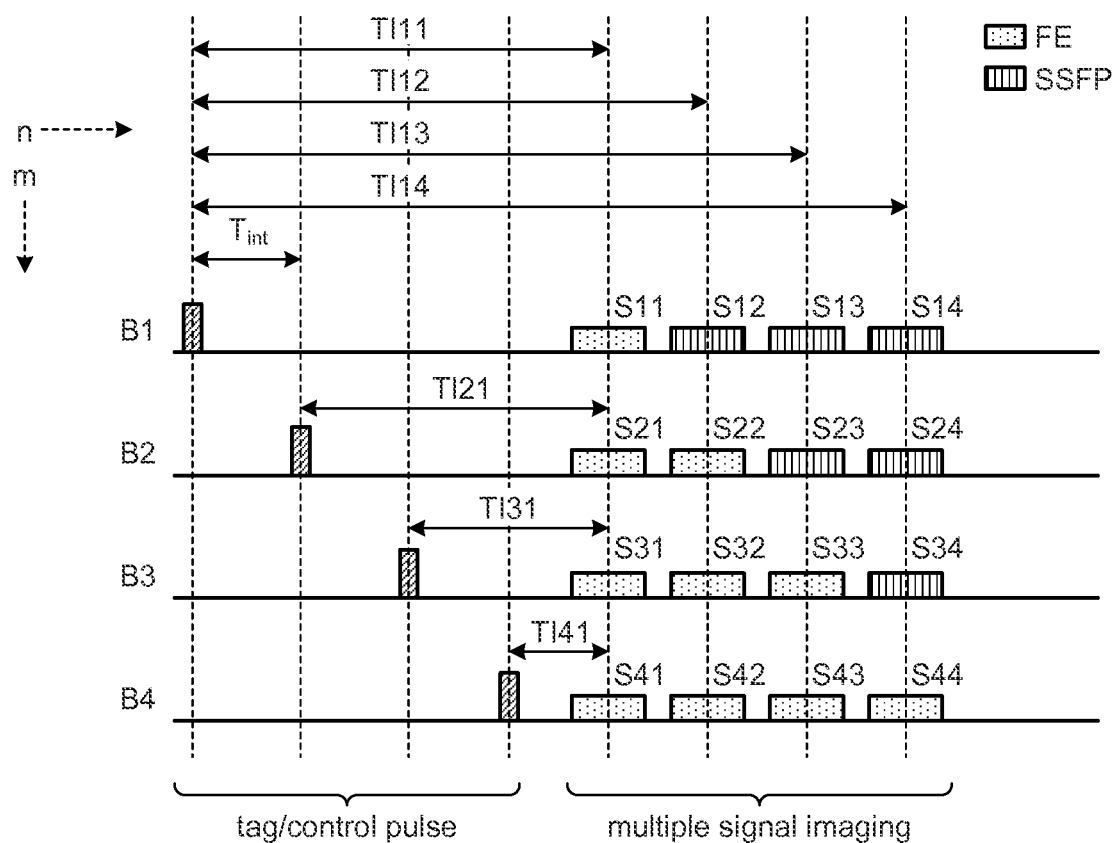
FIG. 22 is a second drawing for explaining the ST-MI-ASL method implemented by the MRI apparatus according to the fourth embodiment.

FIGS. 21 and 22 are drawings for explaining an ST-MI-ASL method implemented by the MRI apparatus according to the fourth embodiment. As illustrated in FIG. 21, for example, the acquiring unit 36c performs a data acquiring process according to the ST-MI-ASL method as many times as M. In that situation, for example, the acquiring unit 36c performs a data acquiring process according to the ST-MI-ASL method as many times as N, while varying the waiting period from the application of the labeling-purpose RF wave to the initial data acquiring process so as to be integer multiples of the predetermined time span $T_{int}$. Further, for example, every time the data acquiring process according to the ST-MI-ASL method is performed, the acquiring unit 36c acquires as many pieces of MR data as N, at each of the points in time later than the application of the labeling-purpose RF wave by the integer multiples of the predetermined time span $T_{int}$. In the fourth embodiment, the waiting period from when the labeling-purpose RF wave is applied, to when the initial data acquiring process is performed, as well as the elapsed time period, for the second data acquiring process, from when the labeling-purpose RF wave is applied, to when the data acquiring process is performed are each referred to as TI.

In this situation, for example, the acquiring unit 36c performs the data acquiring processes according to the ST-MI-PASL method, while varying the waiting period from when the labeling-purpose RF wave is applied, to when the initial data acquiring process is performed, so that each TI expressed as TImn is equal to TI11, TI21, TI31, and TI41 as shown below. After that, for the first time, the acquiring unit 36c performs a data acquiring process after the waiting period TI11 has elapsed. Subsequently, the acquiring unit 36c performs data acquiring processes when TI12, TI13, and TI14 have each elapsed. Further, for the second time, the acquiring unit 36c performs a data acquiring process after the waiting period TI21 has elapsed. Subsequently, the acquiring unit 36c performs data acquiring processes when TI22, TI23, and TI24 have each elapsed. Further, for the third time, the acquiring unit 36c performs a data acquiring process after the waiting period TI31 has elapsed. Subsequently, the acquiring unit 36c performs data acquiring processes when TI32, TI33, and T34 have each elapsed. Further, for the fourth time, the acquiring unit 36c performs a data acquiring process after the waiting period TI41 has elapsed. Subsequently, the acquiring unit 36c performs data acquiring processes when TI42, TI43, and T44 have each elapsed.

$$TI14=7T_{int}$$

$$TI13=TI24=6T_{int}$$

$$TI12=TI23=TI34=5T_{int}$$

$$TI11=TI22=TI33=TI44=4T_{int}$$

$$TI21=TI32=TI43=3T_{int}$$

$$TI31=TI42=2T_{int}$$

$$TI41=1T_{int}$$

Subsequently, after correcting the acquired plurality of pieces MR data, the acquiring unit 36c adds the pieces of data together in groups each having mutually the same elapsed time periods from the application of the RF wave to the data acquiring process. For example, the acquiring unit 36c calculates S(TI) expressing the pieces of MR data to be added together, by using the expressions shown below, where a correction coefficient used for correcting a T1 attenuation dependent on TI is expressed as "a(TI)", and a correction coefficient used for correcting a T1 attenuation dependent on the order "n" in which the data is acquired is expressed as "bn".

$$S(7T_{int})=a(7T_{int})*b4*S14$$

$$S(6T_{int})=a(6T_{int})*\{b3*S13+b4*S24\}/2$$

$$S(5T_{int})=a(5T_{int})*\{b2*S12+b3*S23+b4*S34\}/3$$

$$S(4T_{int})=a(4T_{int})*\{b1*S11+b2*S22+b3*S33+b4*S44\}/4$$

$$S(3T_{int})=a(5T_{int})*\{b1*S21+b2*S32+b3*S43\}/3$$

$$S(2T_{int})=a(2T_{int})*\{b1*S31+b2*S42\}/2$$

$$S(1T_{int})=a(1T_{int})*b1*S41$$

By using this method, as illustrated in FIG. 21, it is possible to obtain the pieces of MR data of which the quantity is equal to M+N−1 and which correspond to the mutually-different TIs. Among these pieces of MR data, the closer to the middle the TI is, the better the SN ratio is. In this situation, when the TI is shorter than the middle, there is no problem because the SN ratio is higher to begin with. However, when the TI is longer than the middle, the SN ratio become lower. The SN ratio for the longest TI is equal to the SN ratio for the MT-SI-PASL method implemented on one TI in a set, because the acquired data is only one piece. For this reason, it is desirable to arrange the labeling-purpose RF wave and the data acquiring process for each $T_{int}$. Further, it is even more desirable to arrange the sets of data acquiring processes performed N times to be M sets corresponding to m sets of independent tags obtained by shifting the waiting period until the initial data acquiring process by $T_{int}$ each time, so that m=n is satisfied. In this situation, m and n may be different from each other.

The time period between the last RF wave (m=M) corresponding to the shortest TI and the data acquiring process performed for the first time (n=1) does not necessarily have to be $T_{int}$. Further, as long as each TI is an integer multiple of $T_{int}$, the integers do not necessarily have to be consecutive. For missing TIs, the TIs are assumed to be zero and considered absent, when the combining calculation is performed.

When an ASL method is used, the longer the TI is, the lower the SN ratio will be. Thus, it is desirable to increase the number of times the addition is performed. However, when the ST-MI-PASL method is used, the later a piece of data is acquired, the lower the SN ratio will be. Thus, it is not a good idea to acquire so many pieces of data. Accordingly, it is possible to improve the processing efficiency even by arranging "n" to be a small value and performing the combining process on m sets of data acquired by using independent RF waves, while discarding pieces of data after the middle, which have a lower SN ratio and correspond to longer TIs.

Further, in the fourth embodiment, when images of the patient are to be acquired by using the imaging method described above, the acquiring unit 36c performs a data acquiring process by using the FE-based readout sequence with respect to the pattern having the shorter waiting period from when the labeling-purpose RF wave is applied, to when the initial data acquiring process is performed, and performs a data acquiring process by using the SSFP-based readout sequence with respect to the pattern having the longer waiting period from when the labeling-purpose RF wave is applied, to when the initial data acquiring process is performed.

For example, as illustrated in FIG. 21, when implementing the ST-MI-ASL pattern four times, while shortening, by $T_{int}$ each time, the waiting period from when the labeling-purpose RF wave is applied, to when the initial data acquiring process is performed, the acquiring unit 36c controls the sequencer 10 so as to perform the data acquiring processes by using the SSFP-based readout sequence with respect to the first- and the second-time patterns and so as to perform the data acquiring processes by using the FE-based readout sequence with respect to the third- and the fourth-time patterns.

Alternatively, for each of the data acquiring processes corresponding to the different patterns, the acquiring unit 36c may use the FE-based readout sequence for data acquiring processes having shorter waiting periods from when the labeling-purpose RF wave is applied, to when the data acquiring process is performed and may use the SSFP-based readout sequence for data acquiring processes having longer waiting periods from when the labeling-purpose RF wave is applied, to when the data acquiring process is performed.

For example, as illustrated in FIG. 22, with respect to the patterns corresponding to the four times, the acquiring unit 36c controls the sequencer 10 so as to use the FE-based readout sequence for the data acquiring processes S11, S21, S22, S31 to S33, and S41 to S44 where the waiting period from when the labeling-purpose RF wave is applied, to when the data acquiring process is performed is equal to or shorter than $4T_{int}$ and so as to use the SSFP-based readout sequence for the data acquiring processes S12 to S14, S23, S24, and S34 where the waiting period from when the labeling-purpose RF wave is applied, to when the data acquiring process is performed is longer than $4T_{int}$.

By using the MRI apparatus according to at least one aspect of the first to the fourth embodiments described above, it is possible to obtain either an MRA image or an MRP image of the entire organ on which the impact made by the magnetization susceptibility effect is smaller and which has a better SN ratio for all the waiting periods TI, than in the example in which a single readout sequence is used. Further, by using the MRI apparatus according to at least one aspect of the first to the fourth embodiments, when images of the arteries in the brain are acquired, for example, it is possible to improve the capability of rendering the blood flows not only in the major arteries but also in the peripheral arteries. Further, by using the MRI apparatus according to at least one aspect of the first to the fourth embodiments, it is possible to obtain a perfusion image having a high SN ratio for a certain tissue part that has a long delay period from when the labeling-purpose RF wave is applied, to when the labeled blood reaches the tissue.

Fifth Embodiment

Next, a fifth embodiment will be explained. In the fifth embodiment, an example will be explained in which images of blood vessels in the head of a patient are to be acquired by using an imaging method by which an imaging region of the patient is divided into a plurality of sectional regions, so that a data acquiring process is performed on each of the plurality of sectional regions. The configuration of the MRI apparatus according to the fifth embodiment is basically the same as the configuration illustrated in FIGS. 1 and 9.

For example, examples of such an imaging method include a multi-slab 3D TOF-MRA method, which is a 3D TOF-MRA method to which the multi-slab method is applied. According to the multi-slab 3D TOF-MRA method, only an imaging region (imaging slab) is set, because instead of applying the labeling-purpose RF wave, the method utilizes a contrast difference between an in-flow effect of blood of which longitudinal magnetization has sufficiently recovered and an inhibiting effect of longitudinal magnetization in a stationary part.

When images of a patient are to be acquired by using the multi-slab 3D TOF-MRA method as described above, the dividing unit 36b divides a spatial range used when the images of the patient are acquired, into at least two ranges on the basis of the sectional regions. Further, of the two ranges resulting from the dividing process performed by the dividing unit 36b, the acquiring unit 36c performs a data acquiring process on the range including major arteries by using a first readout sequence and performs a data acquiring process on the range including peripheral arteries by using a second readout sequence.

Figure 23:
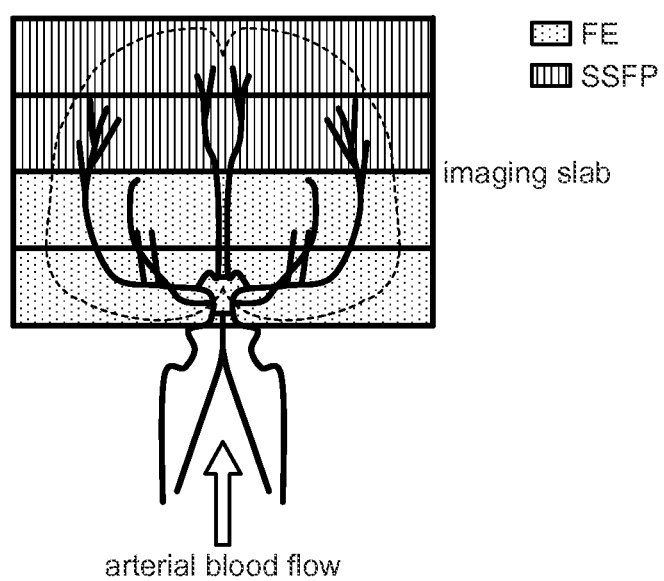
FIG. 23 is a drawing for explaining a multi-slab 3D TOF-MRA method implemented by an MRI apparatus according to a fifth embodiment.

FIG. 23 is a drawing for explaining the multi-slab 3D TOF-MRA method implemented by the MRI apparatus according to the fifth embodiment. As illustrated in FIG. 23, for example, according to the multi-slab 3D TOF-MRA method, the imaging region of the patient is divided into four sectional regions, so that a data acquiring process is performed on each of the sectional regions.

In that situation, for example, the dividing unit 36b divides the spatial range into a range in which the labeled blood flows through major arteries and a range in which the labeled blood flows through peripheral arteries. Further, for example, the acquiring unit 36c controls the sequencer 10 so as to perform the data acquiring process on a major artery part in the vicinity of the circle of Willis by using the FE-based readout sequence that is more resistant to non-uniformity of the magnetic field and so as to perform the data acquiring process on a peripheral artery part such as the parietal region by using the SSFP-based readout sequence that has a higher SN ratio.

With the multi-slab 3D TOF-MRA method described above, a TONE method may be used together which is configured to improve the capability of rendering the peripheral arteries by tilting the flip angle of the RF wave radiated onto the imaging region. Further, the method described above is also applicable to a 2D multi slice method. In that situation, the imaging conditions of the readout sequences may be changed. Although TOF methods basically use GRE, it is also acceptable to change, among the imaging conditions thereof, the inclination in the TONE method in accordance with the blood flow rate within the target slab. In other words, the inclination may be arranged so that the slower the flow rate is, the steeper the inclination is. Further, sets made up of TE and Gradient Moment Nulling (GMN) may selectively be used as "a shorter TE+zeroth-order GMN" and "a longer TE+first-order GMN". It is possible to inhibit lowering of signals caused by phase dispersions, by using the former for a major artery part of the brain or the like where the magnetization susceptibility is high and the flow rate is high and using the latter for a periphery part where the magnetization susceptibility and flow rate are opposite. Further, a condition with a different bandwidth (BW) may be combined. It is possible to inhibit lowering of signals caused by phase dispersions by using a smaller BW for a periphery part so as to improve the SN ratio and using a larger BW for a trunk part.

Sixth Embodiment

Next, a sixth embodiment will be explained. In the sixth embodiment, an example will be explained in which images of blood vessels in the head of a patient are to be acquired by using a multi-slab ASL method in which a multi-slab imaging process is combined with a TOF-MRA method and an ASL-MRA/MRP method. The configuration of the MRI apparatus according to the sixth embodiment is basically the same as the configuration illustrated in FIGS. 1 and 9.

According to the multi-slab ASL method, the images of the patient are acquired by using an imaging method by which an imaging region of the patient is divided into a plurality of sectional regions, so that a data acquiring process is performed, with respect to each of the sectional regions, after a predetermined waiting period has elapsed since an RF wave for the purpose of labeling fluid flowing into the sectional region is applied to a labeled region positioned away from the sectional region by a predetermined distance on the upstream side of the fluid.

Figure 24:
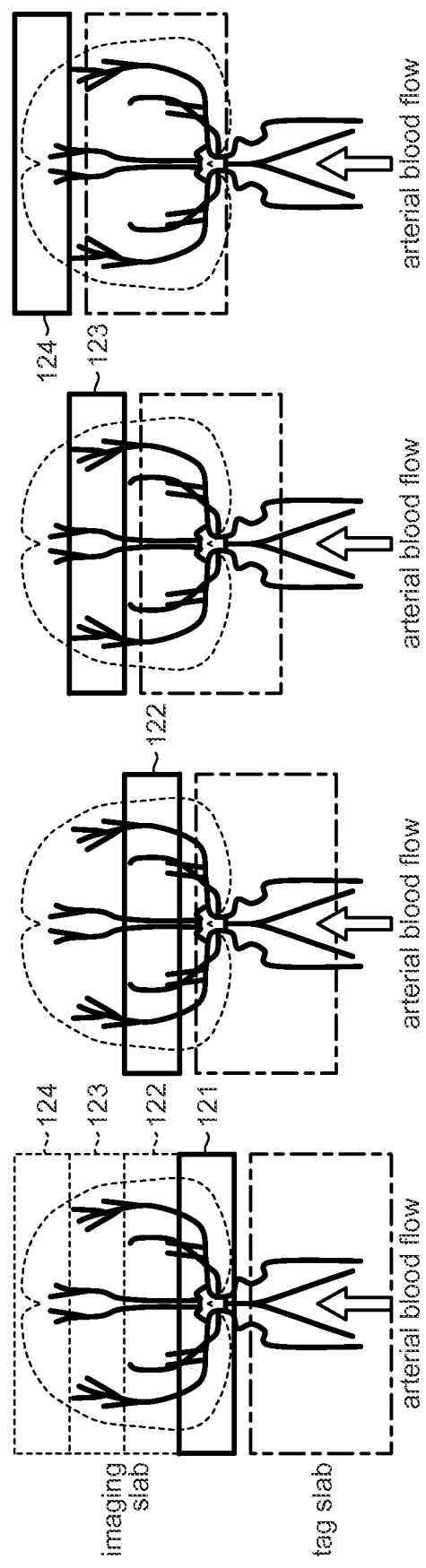
FIG. 24 is a drawing for explaining a multi-slab ASL method implemented by an MRI apparatus according to a sixth embodiment.

FIG. 24 is a drawing for explaining the multi-slab ASL method implemented by the MRI apparatus according to the sixth embodiment. As illustrated in FIG. 24, for example, according to the multi-slab ASL method, the imaging region (imaging slab) is divided into four sectional regions 121 to 124. After that, to acquire data from each of the sectional regions, a labeling-purpose RF wave is applied to a tag region (tag slab) that is positioned away from the sectional region by the predetermined distance on the upstream side of the blood flow. In other words, according to the multi-slab ASL method, while moving the sectional region on which the data acquiring process is performed, the tag region is moved so as to follow the sectional region while keeping a predetermined distance therefrom, in conjunction with the moving of the sectional region. Although not illustrated in FIG. 24, the control region is also moved so as to follow the sectional region in each position, while keeping the relative position the same.

By using the multi-slab ASL method described above, it is possible to improve the SN ratio compared to the situation where the position of the tag region with respect to the plurality of sectional regions is fixed on the upstream side of the entire imaging region, because the more downstream a sectional region is positioned, the shorter time it takes for the labeled blood to reach the sectional region. For this reason, without the need to prolong the waiting period TI from when the labeling-purpose RF wave is applied, to when the data acquiring process is performed, it is also possible to render blood vessels (MRA) and perfusion (MRP) that are positioned in a sectional region distant from the tag region.

When images of blood vessels in the head of a patient are to be acquired by using the multi-slab ASL method described above, for example, the dividing unit 36b divides the imaging region into at least to ranges on the basis of the sectional regions. Further, of the ranges resulting from the dividing process performed by the dividing unit 36b, the acquiring unit 36c performs a data acquiring profess on the range including major arteries by using a first readout sequence and performs a data acquiring process on the range including peripheral arteries by using a second readout sequence.

For example, as illustrated in FIG. 24, of the four sectional regions, the acquiring unit 36c performs data acquiring processes on the sectional regions 121 and 122 that include major arteries and that are positioned on the upstream side, by using the FE-based readout sequence. In contrast, the acquiring unit 36c performs data acquiring processes on the sectional regions 123 and 124 that include peripheral arteries and that are positioned on the downstream side, by using the SSFP-based readout sequence. As a result, it is possible to render the blood vessels in the head of the patient in an excellent manner in the entire region.

By using the MRI apparatus according to at least one aspect of the fifth and the sixth embodiments described above, without the need to prolong the imaging period, it is possible to obtain an image on which the impact made by the magnetization susceptibility effect is smaller and which has a better SN ratio than in the example in which a single readout sequence is used. Further, when the images of the arteries in the brain are acquired, for example, by using the MRI apparatus according to at least one aspect of the fifth and the sixth embodiments, it is possible to improve the capability of rendering the blood flows not only in the major arteries, but also in the peripheral arteries.

Seventh Embodiment

Next, a seventh embodiment will be explained. In the seventh embodiment, an example will be explained in which images of a patient are acquired by using a diffusion imaging method. The configuration of the MRI apparatus according to the seventh embodiment is basically the same as the configuration illustrated in FIGS. 1 and 9.

In recent years, the diffusion imaging method has been used not only for a cranial nervous region but also for any organ in the entire human body for the purpose of detecting tumors. Generally speaking, to implement the diffusion imaging method, an SE-based readout sequence using single shot SE-EPI (S-EPI) is used.

In this regard, it is known that non-uniformity of the magnetic field is larger at the basal part of the brain and the spine in the neck or the chest such as the cerebellum and the frontal spine for the cranial nerve region, as well as the lungs, a part of the liver positioned closed to the lungs, and the parts positioned close to the rectum or the colon for the abdominal region. However, an S-EPI readout sequence is not resistant to non-uniformity of the magnetic field. Thus, in some situations, a large distortion may occur, or a signal that is supposed to be rendered in a different voxel may be rendered in the same voxel as another signal in an overlapping manner.

Further, other examples of readout sequences that can be used in the diffusion imaging method include FSE-based readout sequence (e.g., Half-Fourier Single shot Turbo spin Echo [HASTE]) and a multi-shot EPI (M-EPI) readout sequence by which a phase difference between shots due to movements is corrected by simultaneously acquiring a navigator echo. Further, other examples include non-Cartesian-type PROPELLER (JET), and a radial-type, which differ in the trajectory of the k-space. However, for the reason that these readout sequences have a lower SN ratio per unit time period than an S-EPI readout sequence, it is difficult to take images of a large region such as the entire human body by using one type of readout sequence or one type of imaging conditions.

When images of a subject are to be acquired by using the diffusion imaging method described above, the dividing unit 36b divides a spatial range used when the images of the patient are acquired, into at least two ranges, on the basis of a distribution of static magnetic field intensities (B0). For example, the dividing unit 36b divides the imaging region used when the images of the patient are acquired, into two ranges, on the basis of a predetermined threshold value related to a standard deviation of delta B0.

Further, of the two ranges resulting from the dividing process performed by the dividing unit 36b, the acquiring unit 36c performs a data acquiring process on the range having the larger non-uniformity of the static magnetic field by using a first readout sequence and performs a data acquiring process on the range having the smaller non-uniformity of the static magnetic field by using a second readout sequence. For example, of the two ranges, the acquiring unit 36c determines the range having the larger standard deviation of delta B0 as the range having the larger non-uniformity of the static magnetic field and determines the range having the smaller standard deviation of delta B0 as the range having the smaller non-uniformity of the static magnetic field. In this situation, if the imaged target is the head, the range having the larger non-uniformity of the static magnetic field corresponds to the neck or the basal part of the brain. In contrast, the range having the smaller non-uniformity of the static magnetic field corresponds to the parietal region or the like. As another example, if the imaged target is the abdomen, the range having the higher intensity of the static magnetic field corresponds to the lungs or a part of the liver positioned close to the lungs. In contrast, the range having the lower intensity of the static magnetic field corresponds to retroperitoneal organs or the like.

For example, the acquiring unit 36c performs a data acquiring process on the range having the larger non-uniformity of the static magnetic field by using the FSE-based readout sequence, which is more resistant to distortions. In contrast, the acquiring unit 36c performs a data acquiring process on the range having the smaller non-uniformity of the static magnetic field by using the S-EPI-based readout sequence, which is not as resistant to distortions as the FSE-based readout sequence but has a higher SN ratio than the FSE-based readout sequence.

Alternatively, for example, the acquiring unit 36c may perform a data acquiring process on the range having the larger non-uniformity of the static magnetic field by implementing the PROPELLER (JET) method and using the FSE-based readout sequence and may perform a data acquiring process on the range having the smaller non-uniformity of the static magnetic field by using the S-EPI-based readout sequence.

Alternatively, for example, the acquiring unit 36c may perform a data acquiring process on the range having the larger non-uniformity of the static magnetic field by using imaging conditions that are more resistant to distortions and may perform a data acquiring process on the range having the smaller non-uniformity of the static magnetic field by using imaging conditions that have a higher SN ratio, while using either mutually the same readout sequence or mutually-different readout sequences. In that situation, for example, the acquiring unit 36c uses imaging conditions including a higher SENSE-factor as the imaging conditions that are more resistant to distortions and uses imaging conditions including a lower SENSE-factor as the imaging conditions having a higher SN ratio.

Alternatively, for example, while using mutually the same EPI readout sequence, the acquiring unit 36c may perform a data acquiring process on the range having the larger non-uniformity of the static magnetic field by using imaging conditions including a larger number of shots and may perform a data acquiring process on the range having the smaller non-uniformity of the static magnetic field by using imaging conditions including a smaller number of shots. For example, the acquiring unit 36c performs the data acquiring process on the range having the larger non-uniformity of the static magnetic field by using the M-EPI readout sequence and performs the data acquiring process on the range having the smaller non-uniformity of the static magnetic field by using the S-EPI readout sequence.

Further, when the diffusion imaging method is used, it is known that distortions caused by an eddy current become larger, when an MPG intensity or a b-value becomes larger. To cope with this situation, for example, the acquiring unit 36c may perform a data acquiring process on the range having the larger non-uniformity of the static magnetic field by using imaging conditions in which the MPG intensity or the b-value is arranged to be smaller. In contrast, the acquiring unit 36c may perform a data acquiring process on the range having the smaller non-uniformity of the static magnetic field by using imaging conditions in which the MPG intensity or the b-value is arranged to be larger.

Eighth Embodiment

Next, an eighth embodiment will be explained. In the eighth embodiment, an example in which quantitative value images (parameter images) are acquired will be explained. The configuration of the MRI apparatus according to the eighth embodiment is basically the same as the configuration illustrated in FIGS. 1 and 9.

In recent years, because it becomes easier to make comparisons among different medical examinations, it has been a common practice to express in images various parameters related to MRI (e.g., T1, T2, the proton density, ADC, the blood flow amount, chemical shifts, magnetization susceptibility, temperatures).

When images of a patient are to be acquired by using an imaging method for spatially mapping a predetermined quantitative value as described above, the dividing unit 36b divides either a temporal range or a spatial range used when the images of the patient are acquired, in accordance with characteristics of the target site. Further, with respect to each of the plurality of ranges resulting from the dividing process performed by the dividing unit 36b, the acquiring unit 36c changes either the type or the imaging conditions of the readout sequence used for performing the data acquiring process, in accordance with the characteristics of the target site included in the range.

The MRI apparatuses according to the first to the eighth embodiments have thus been explained. However, possible embodiments are not limited to these examples. For instance, in the embodiments described above, the example is explained in which the dividing unit 36b divides either the temporal range or the spatial range used when the images of the patient are acquired, on the basis of the anatomical information related to the site serving as the imaged target. However, the dividing method is not limited to this example.

For example, the dividing unit 36b may divide either the temporal range or the spatial range used when images of a patient are acquired, on the basis of a distribution of static magnetic field intensities measured for a shimming purpose. For example, the dividing unit 36b divides either the temporal range or the spatial range into at least two ranges, on the basis of a statistical value such as the standard deviation or an average value related to delta B0. In that situation, the dividing unit 36b sets a predetermined threshold value with respect to the statistical value related to delta B0 and divides either the temporal range or the spatial range by using the threshold value as the boundary.

Alternatively, for example, the dividing unit 36b may divide either the temporal range or the spatial range used when images of a patient are acquired, on the basis of an image used for the purpose of determining the position of the imaging region. For example, the dividing unit 36b divides either the temporal range or the spatial range by using, as the boundary, a position specified by the operator within an axial image, a coronal image, or a sagittal image acquired as a position determining purpose image. For example, if a 3D TOF image has already been obtained, the dividing unit 36b uses the 3D TOF image as the position determining purpose image. If the 3D TOF image has not yet been obtained, the dividing unit 36b may use an image obtained by implementing a two-dimensional Phase Contrast (2D PC) method as the position determining purpose image.

Further, in the embodiments described above, the example is mainly explained in which the FE-based readout sequence and the SSFP-based readout sequence are used; however, the types of readout sequences are not limited to this example. In other words, of the two or more ranges resulting from the dividing process performed by the dividing unit 36b, the acquiring unit 36c selectively uses different types of readout sequences as appropriate, in accordance with the site serving as the imaged target and the imaging purpose. For example, if it is possible to calculate the SN ratio for one of the two ranges, the acquiring unit 36c uses, for the one range, such a readout sequence that has a higher SN ratio per unit acquisition period than the readout sequence used for the other range. As another example, if it is possible to calculate the spatial resolution for one of the two ranges, the acquiring unit 36c uses, for the one range, such a readout sequence that has a higher spatial resolution than the readout sequence used for the other range. As yet another example, if one of the two ranges is less resistant to the impact made by non-uniformity of the static magnetic field, the acquiring unit 36c uses, for the one range, such a readout sequence that is more resistant to non-uniformity of the static magnetic field than the readout sequence used for the other range.

Further, of the two or more ranges resulting from the dividing process performed by the dividing unit 36b, the acquiring unit 36c may selectively use various imaging conditions of the readout sequences as appropriate, in accordance with the site serving as the imaged target and the imaging purpose. For example, if it is possible to calculate the SN ratio for one of the two ranges, the acquiring unit 36c uses, for the one range, such imaging conditions that have a higher SN ratio per unit acquisition period than the imaging conditions used for the other range. As another example, if it is possible to calculate the spatial resolution for one of the two ranges, the acquiring unit 36c uses, for the one range, such imaging conditions that have a higher spatial resolution than the imaging conditions used for the other range. As yet another example, if one of the two ranges is less resistant to the impact made by non-uniformity of the static magnetic field, the acquiring unit 36c uses, for the one range, such imaging conditions that are more resistant to non-uniformity of the static magnetic field than the imaging conditions used for the other range.

In the embodiments described above, the example is mainly explained in which the images of the blood vessels in the head of the patient are acquired; however, the site serving as the imaged target does not necessarily have to be the head. For example, the site serving as the imaged target may be any other site such as the abdomen. Further, in the embodiments described above, the example is mainly explained in which the blood flow images are generated; however, the fluid serving as the imaged target does not necessarily have to be blood. For example, the fluid serving as the imaged target may be any other fluid such as Cerebrospinal Fluid (CSF).

As noted above, the imaging conditions of the readout sequences are parameter values of the imaging parameters that are used when images of a predetermined imaging region are acquired. In other words, using different imaging conditions means using different parameter values for the imaging parameters that are used for acquiring the data in a certain slice position. For example, when an imaging region is divided into temporal ranges, the data acquiring processes are performed while varying the parameter values of the imaging parameters of the readout sequence for each of the temporal ranges resulting from the division, with respect to mutually the same slice position. In another example, when an imaging region is divided into spatial ranges, the data acquiring processes are performed while varying the parameter values of the imaging parameters of the readout sequence for each of the spatial ranges resulting from the division, with respect to mutually-different slice positions.

By using the MRI apparatus according to at least one aspect of the first to the eighth embodiments described above, it is possible to obtain an MRI image having a better spatial resolution and a better SN ratio and having fewer artifacts than in the example where images are acquired by using a single type of readout sequence or a single set of imaging conditions, for the entire part including the mutually-different temporal or spatial ranges, while spending substantially the same amount of imaging period.

In the first to the eighth embodiments described above, the examples are explained in which the imaging region is divided into either the temporal ranges or the spatial ranges, so as to change one or both of the type of readout sequence and the imaging conditions for each of the ranges resulting from the division. However, possible embodiments are not limited to these examples. For instance, it is also acceptable to change, for each of the ranges resulting from the division, conditions for a pre-pulse that is applied prior to the readout sequence.

As another example, it is also acceptable to change a tag condition for the labeling-purpose RF pulse used in the ASL method. For example, as explained in the sixth embodiment, when images of a patient are to be acquired by using the multi-slab ASL method, the acquiring unit moves the region to which the labeling-purpose RF pulse is applied (i.e., the tag region) so as to follow the moving of the sectional region on which the data acquiring is performed, for each of the ranges divided temporally or spatially. In that situation, for example, the acquiring unit changes the absolute position of the tag region, in such a manner that the relative position between the tag region and the sectional region remains unchanged.

Further, for example, when images are to be acquired by using adiabatic pulses, it is also acceptable to change the RF power (the flip angle) of inversion pulses (i.e., adiabatic pulses), for each of the ranges resulting from the division. The adiabatic pulses theoretically have such characteristics that the longitudinal magnetization thereof does not turn by more than 180 degrees even if the RF power (the flip angle) is larger than the level that causes longitudinal magnetization to decline by 180 degrees. However, when the RF power is larger, the load on an RF amplifier used for amplifying the RF wave to be transmitted to the transmission RF coil also becomes larger. Thus, when a plurality of adiabatic pulses are applied during a short period of time, it is necessary to distribute the RF power in units of appropriate size in consideration of the duty cycle. For example, in consideration of the fact that sensitivity levels of transmission RF coil are not uniform, the acquiring unit exercises control so that, of the ranges resulting from the division, the flip angle of the inversion pulse is set to 300 degrees for the range positioned farther from the center of the RF coil where the transmission RF power is lower, whereas the flip angle of the inversion pulse is set to 180 degrees for the range positioned closer to the center of the RF coil where the transmission RF power is at a sufficient level.

By using the MRI apparatus according to at least one aspect of the embodiments described above, it is possible to obtain the images having higher quality in accordance with the site serving as the imaged target and the imaging purpose.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging (MRI) apparatus comprising:
   MRI processing circuitry configured to
   divide, when performing a data acquiring process at a plurality of different timings by varying a waiting period until starting the data acquiring process after applying an RF wave to label fluid flowing into an imaging region of a patient, the plurality of different timings into at least two temporal ranges of timings; and perform the data acquiring process at a timing included in a first range of the temporal ranges by using a first readout sequence and perform the data acquiring process at a timing included in a second range of the temporal ranges by using a second readout sequence that is different from the first readout sequence in terms of one or both of a type of sequence and an imaging condition, wherein the processing circuitry is configured to change, when detecting that the labeled fluid has reached a predetermined position in the imaging region, the readout sequence used for performing the data acquiring process from the first readout sequence to the second readout sequence.

2. The magnetic resonance imaging apparatus according to claim 1, wherein, the processing circuitry is configured to divide, when images of a head of the patient are to be acquired by using an imaging method by which blood serving as the fluid is labeled, the plurality of the timings into a range in which the labeled blood flows through a major artery and a range in which the labeled blood flows through a peripheral artery.

3. The magnetic resonance imaging apparatus according to claim 1, wherein the processing circuitry is configured to divide, when images of the patient are to be acquired by using an imaging method for spatially mapping predetermined quantitative values, the plurality of timings in accordance with characteristics of a target site.

4. The magnetic resonance imaging apparatus according to claim 1, wherein the second readout sequence has a higher Signal-to-Noise (SN) ratio per unit acquisition period than the first readout sequence.

5. The magnetic resonance imaging apparatus according to claim 1, wherein the first readout sequence either has a higher spatial resolution or is more resistant to non-uniformity of a static magnetic field than the second readout sequence.

6. The magnetic resonance imaging apparatus according to claim 1, wherein the processing circuitry is configured to combine the images together, after performing at least one correcting process selected from among a gain correction, a T1 relaxation correction, and an image interpolation, on one or both of the image generated from the data acquired by using the first readout sequence and the image generated from the data acquired by using the second readout sequence.

7. The magnetic resonance imaging apparatus according to claim 1, wherein the processing circuitry is configured to divide the plurality of timings on a basis of one of the following: anatomical information related to a site serving as an imaged target; a distribution of static magnetic field intensities measured for a shimming purpose; and an image used for a purpose of determining a position of the imaging region.

8. The magnetic resonance imaging apparatus according to claim 1, wherein the processing circuitry is further configured to combine an image generated from data acquired by using the first readout sequence with an image generated from data acquired by using the second readout sequence.

9. A magnetic resonance imaging (MRI) apparatus comprising:

MRI processing circuitry configured to divide, when performing at a plurality of different timings a pattern in which a data acquiring process is started when a waiting period has elapsed since applying an RF wave to label fluid flowing into an imaging region by varying the waiting period, the plurality of timings into at least two temporal ranges of timings; and perform the data acquiring process at a timing included in a first range of the temporal ranges by using the first readout sequence and perform a data acquiring process at a timing included in a second range of the temporal ranges by using a second readout sequence that is different from the first readout sequence in terms of one or both of a type of sequence and an imaging condition, wherein the processing circuitry is configured to change, when detecting that the labeled fluid has reached a predetermined position in the imaging region, the readout sequence used for performing the data acquiring process from the first readout sequence to the second readout sequence.

10. A magnetic resonance imaging (MRI) apparatus comprising:

MRI processing circuitry configured to divide, when performing a data acquiring process at a plurality of different timings by varying a waiting period until starting the data acquiring process after applying an RF wave to label fluid flowing into an imaging region of a patient, the imaging region of the patient into at least two spatial ranges on a basis of the waiting period; and perform the data acquiring process on a first range of the spatial ranges by using a first readout sequence and perform the data acquiring process on a second range of the spatial ranges by using a second readout sequence that is different from the first readout sequence in terms of one or both of a type of sequence and an imaging condition;

wherein the processing circuitry is configured to change, when detecting that the labeled fluid has reached a predetermined position in the imaging region, the readout sequence used for performing the data acquiring process from the first readout sequence to the second readout sequence.

11. The magnetic resonance imaging apparatus according to claim 10, wherein, the processing circuitry is configured to divide, when images of a head of the patient are to be acquired by using an imaging method by which blood serving as the fluid is labeled, the imaging region into a range in which the labeled blood flows through a major artery and a range in which the labeled blood flows through a peripheral artery.

12. The magnetic resonance imaging apparatus according to claim 10, wherein the imaging region includes a plurality of sectional regions, and the processing circuitry is configured to divide the plurality of sectional regions into the at least two spatial ranges.

13. The magnetic resonance imaging apparatus according to claim 10, wherein the first range is a range of shorter waiting period in the at least two spatial ranges and the second range is a range of longer waiting period in the at least two spatial ranges.

14. The magnetic resonance imaging apparatus according to claim 10, wherein the processing circuitry is further configured to generate an image of the imaging region by combining an image generated from data acquired by using the first readout sequence with an image generated from data acquired by using the second readout sequence.

15. A magnetic resonance imaging (MRI) apparatus comprising:

MRI processing circuitry configured to divide, when acquiring images of a patient using a diffusion imaging method, the imaging region of the patient into at least two spatial ranges, on a basis of a distribution of static magnetic field intensities, and perform a data acquiring process on a range having larger non-uniformity of a static magnetic field by using a first readout sequence and perform a data acquiring process on a range having smaller non-uniformity of the static magnetic field by using a second readout sequence that is different from the first readout sequence in terms of one or both of a type of sequence and an imaging condition.

16. A magnetic resonance imaging (MRI) apparatus comprising:

MRI processing circuitry configured to divide, when performing a data acquiring process at a plurality of different timings by varying a waiting period until starting the data acquiring process after applying an RF wave to label fluid flowing into an imaging region of a patient, the plurality of different timings into at least two temporal ranges or the imaging region of the patient into at least two spatial ranges, on a basis of a distribution of static magnetic field intensities, perform data acquiring processes on an entirety of the imaging region by using each of a first readout sequence and a second readout sequence that is different from the first readout sequence in terms of one or both of a type of sequence and an imaging condition, and combine an image in a first range out of the image generated from the data acquired by using the first readout sequence with an image in a second range out of the image generated from the data acquired by using the second readout sequence.

\* \* \* \* \*